(12) United States Patent
Frendéus et al.

(10) Patent No.: US 7,943,744 B2
(45) Date of Patent: May 17, 2011

(54) ICAM-1 BINDING ANTIBODIES

(75) Inventors: Björn Frendéus, Landskrona (SE); Roland Carlsson, Lund (SE); Anne-Christine Carlsson, legal representative, Lund (SE)

(73) Assignee: BioInvent International AB, Lund (SE)

( * ) Notice: Subject to any disclaimer, the term of this patent is extended or adjusted under 35 U.S.C. 154(b) by 0 days.

(21) Appl. No.: 12/097,193

(22) PCT Filed: Dec. 8, 2006

(86) PCT No.: PCT/EP2006/012065
§ 371 (c)(1),
(2), (4) Date: Oct. 2, 2008

(87) PCT Pub. No.: WO2007/068485
PCT Pub. Date: Jun. 21, 2007

(65) Prior Publication Data
US 2009/0087427 A1     Apr. 2, 2009

(30) Foreign Application Priority Data

Dec. 12, 2005  (GB) .................................. 0525214.3

(51) Int. Cl.
C07K 16/00 (2006.01)
C12P 21/08 (2006.01)
A61K 39/395 (2006.01)
A61K 39/00 (2006.01)
G01N 33/53 (2006.01)

(52) U.S. Cl. ............. 530/388.15; 424/130.1; 424/142.1; 424/152.1; 530/388.1; 435/7.1

(58) Field of Classification Search .................. None
See application file for complete search history.

(56) References Cited

U.S. PATENT DOCUMENTS
6,416,958 B2   7/2002   Vidovic

FOREIGN PATENT DOCUMENTS
WO    WO 91/09967    *    7/1991
WO    WO 2004/023140    3/2004

OTHER PUBLICATIONS

Burgess, Shaheen, Ravera, Jaye, Donohue, and Winkles. Possible dissociation of the heparin binding and mitogenic activities of heparin-binding (acidic fibroblast) growth factor-1 from it's receptor binding activities by site directed mutagenesis of a single lysine residue. Journal of Cell Biology, 1990. vol. 111,pp. 2129-2138.*
Lazar, Watanabe, Dalton, and Sporn. Transforming growth factor alpha: mutation of aspartic acid 47 and leucine 48 results in different biological activities. Molecular and Cellular Biology, 1988. vol. 8, pp. 1247-1252.*
Rudikoff, Giusti, Cook, and Scharff. Single amino acid substitution altering antigen-binding specificity. Proceedings of the National Academy of Sciences, 1982. vol. 79, pp. 1979-1983.*
Mac Callum, Martin, and Thornton. Antibody-antigen interations: contact analysis and binding site topography. Journal of Molecular Biology, 1996. vol. 262, pp. 732-745.*
De Pascalis, Iwahashi, Tamura, Padlan, Gonzales, Santos, Giuliano, Schuck, Schlom, and Kashmiri. Grafting of abbreviated complementarity determining regions containing specificity determining residues essential for ligand contact to engineer a less immunogenic humanzied monoclonal antibody. Journal of Immunology, 2002. vol. 169, pp. 3076-3084.*
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*
Vajdos, Adams, Breece, Presta, De Vos, and Sidhu. Comprehensive functional maps of the antigen-binding site of an Anti-ErbB2 antibody obtained by shotgun scanning mutagenesis. Journal of Molecular Biology, 2002. vol. 320, pp. 415-428.*
Holm, Jafari, and Sundstrom. Functional mapping and single chain construction of the anti-cytokeratin 8 monoclonal antibody TS1. Molecular Immunology, 2007. vol. 44, pp. 1075-1084.*
Chen, Wiesmann, Fuh, Li, Christinger, Mc Kay, De Vos, and Lowman. Selection and analysis of an optimized anti-VEGF antibody: crystal structure of an affinity matured Fab in complex with antigen. Journal of Molecular Biology, 1999. vol. 293, pp. 865-881.*
Wu, Nie, Huse, and Watkins. Humanization of a murine monoclonal antibody by simultaneous optimization of framework and CDR residues. Journal of Molecular Biology, 1999. vol. 294, pp. 151-162.*
Lonberg. Human antibodies from transgenic animals. Nature Biotechnology, 2005. vol. 23, pp. 1117-1125.*
Aalinkeel et al., "Gene Expression of Angiogenic Factors Correlates with Metastatic Potential of Prostate Cancer Cells," *Cancer Res.*, 2004, 64:5311-5321.
Bai et al., "Antigenic drift as a mechanism for tumor evasion of destruction by cytolytic T lymphocytes," *J. Clin. Invest.*, 2003, 111(10):1487-1496.
Borrebaeck and Carlsson, "Human therapeutic antibodies," *Curr. Opin. Pharmacol.*, 2001, 1:404-408.
Brekke and Sandlie, "Therapeutic Antibodies for Human Diseases at the Dawn of the Twenty-First Century," *Nat. Rev. Drug Discov.*, 2003, 2:52-62.
Brix et al., "Extracellularly Occurring Histone H1 Mediates the Binding of Thyroglobulin to the Cell Surface of Mouse Macrophages," *J. Clin. Invest.*, 1998, 102:283-293.
Budagyan et al., "Anti-ICAM-1 mAb inhibits apoptosis of thymocytes induced by human thymic stromal cells (HTSC) line," *Tissue Antigens*, 1996, 48(4-2):359, Abstract No. AS-3-02 and 6th International Workshop and conference on Human Leukocyte Differentiation Antigens, Kobe, Japan, Nov. 10-14, 1996.

(Continued)

Primary Examiner — Anne M. Gussow
(74) Attorney, Agent, or Firm — Fish & Richardson P.C.

(57) ABSTRACT

The invention provides binding molecules, including antibody molecules which selectively bind to a cell surface antigen of a target cell, and wherein the binding molecules, on binding the cell surface antigen, induce apoptosis of the target cell. There is also provided methods of and pharmaceutical compositions for apoptosis induction and uses thereof.

19 Claims, 19 Drawing Sheets

OTHER PUBLICATIONS

Figure 1:
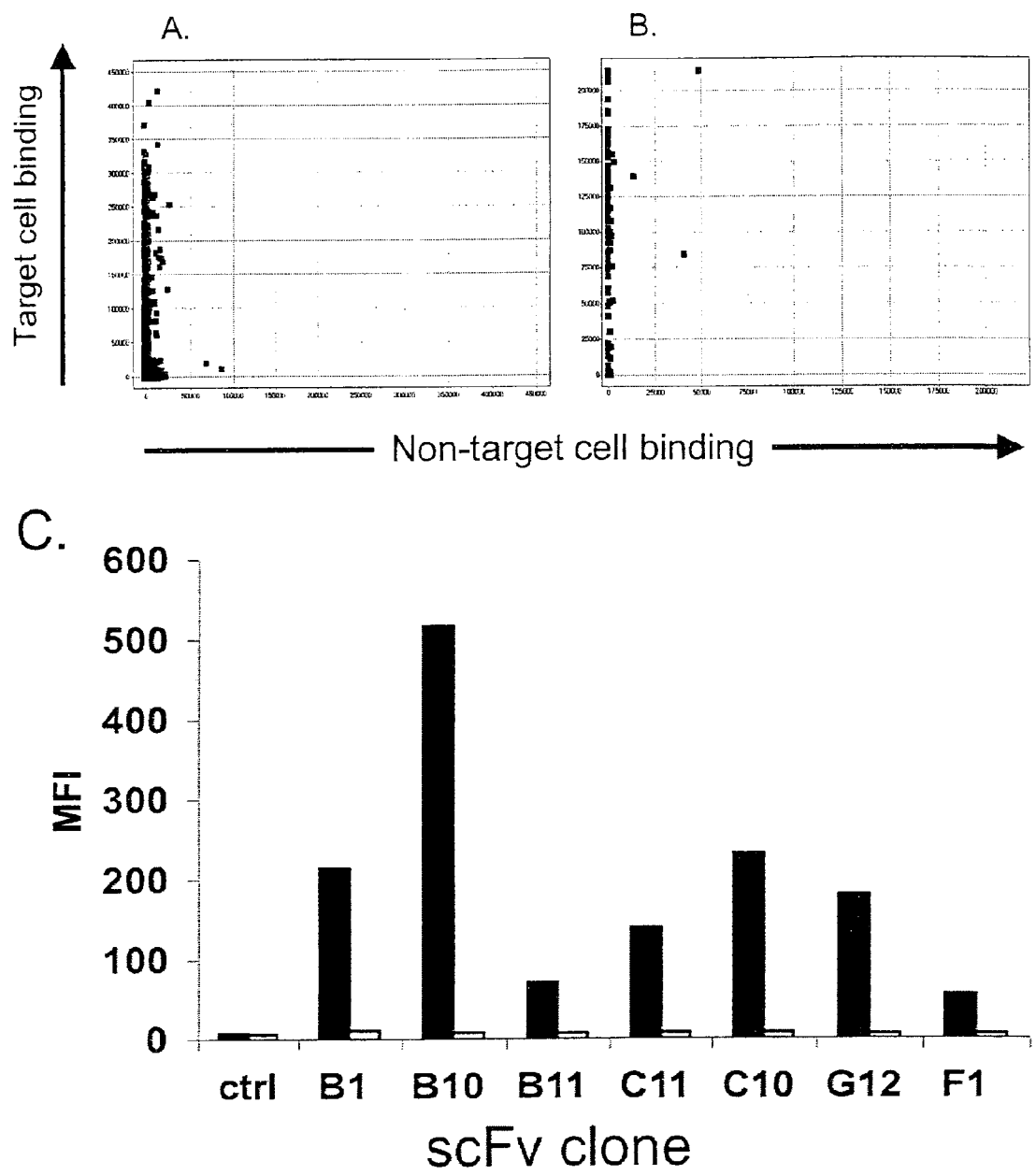

Bylund and Yamamura, "Methods for Receptor Binding," *Methods in Neurotransmitter Receptor Analysis*, 1990, Chapter 1, New York: Raven Press Ltd.

Cerutti et al., "CD40 Ligand and Appropriate Cytokines Induce Switching to IgG, IgA, and IgE and Coordinated Germinal Center and Plasmacytoid Phenotypic Differentiation in a Human Monoclonal IgM⁺IgD⁺ B Cell Line," *J. Immunol.*, 1998, 160:2145-2157.

Clackson et al., "Making antibody fragments using phage display libraries," *Nature*, 1991, 352:624-628.

Coleman et al., "The Fc portion of UV3, an anti-CD54 monoclonal antibody, is critical for its antitumor activity in SCID mice with human multiple myeloma or lymphoma cell lines," *J. Immunol.*, 2006, 29(5):489-498.

Cosimi et al., "In Vivo Effects of Monoclonal Antibody to ICAM-1 (CD54) in Nonhuman Primates with Renal Allografts," *J. Immunol.*, 1990, 144(12):4604-4612.

Daibata et al., "The Establishment of Epstein-Barr Virus Nuclear Antigen-Positive (SP-50B) and Epstein-Barr Virus Nuclear Antigen-Negative (SP-53) Cell Lines with t(11;14)(q13;q32) Chromosome Abnormality From an Intermediate Lymphocytic Lymphoma," *Cancer*, 1989, 64:1248-1253.

Doyle et al., "Specific blockade by CD54 and MHC II of CD40-mediated signaling for B cell proliferation and survival," *Experimental Cell Research*, 2001, 265(2):312-318.

Edvardsson et al., "A proteome analysis of livers from obese (ob/ob) mice treated with the peroxisome proliferator WY14,643," *Electrophoresis*, 1999, 20:935-942.

Fransson et al., "Rapid induction of apoptosis in B-cell lymphoma by functionally isolated human antibodies," *Int. J. Cancer*, 2006, 119(2):349-358.

Griffiths et al., "Human anti-self antibodies with high specificity from phage display libraries," *EMBO J.*, 1993, 12(2):725-734.

Grothey et al., "Serum levels of soluble intercellular adhesion molecule-1 (ICAM-1, CD54) in patients with non-small-cell lung cancer: correlation with histological expression of ICAM-1 and tumour stage," *Br. J. Cancer*, 1998, 77(5):801-807.

Hallbom and Carlsson, "Automated Screening Procedure for High-Throughput Generation of Antibody Fragments," *BioTechniques*, 2002, 33:S30-S37.

Harlow et al. (eds.), "Monoclonal Antibodies," *Antibodies A Laboratory Manual*, 1988, Chapter 6, Cold Spring Harbor Laboratory; Cold Spring Harbor, N.Y.

Haug et al., "A Phase I Trial of Immunosuppression with Anti-ICAM-1 (CD54) mAb in Renal Allograft Recipients," *Transplantation*, 1993, 55(4):766-773.

Högbom et al., "Structural basis for recognition by an in vitro evolved affibody," *Proc. Natl. Acad. Sci USA*, 2003, 100(6):3191-3196.

Huang et al., "Anti-CD54 (ICAM-1) Has Antitumor Activity in SCID Mice with Human Myeloma Cells," *Cancer Res.*, 1995, 55:610-616.

Huang et al., "Cytotoxicity of a Novel Anti-ICAM-1 Immunotoxin on Human Myeloma Cell Lines," *Hybridoma*, 1993, 12(6):661-675.

Kavanaugh et al., "Treatment of Refractory Rheumatoid Arthritis with A Monoclonal Antibody to Intercellular Adhesion Molecule 1," *Arthritis Rheum.*, 1994, 37(7):992-999.

Kennedy et al., "Incidence and nature of CD20-negative relapses following rituximab therapy in aggressive B-cell non-Hodgkin's lymphoma: a retrospective review," *Br. J. Haematol.*, 2002, 119:412-416.

Kim et al., "Transforming Growth Factor-β1 Induces Apoptosis through Fas Ligand-independent Activation of the Fas Death Pathway in Human Gastric SNU-620 Carcinoma Cells," *Mol. Biol. Cell*, 2004, 15:420-434.

Kwak et al., "Induction of Immune Responses in Patients with B-Cell Lymphoma Against the Surface-Immunoglobulin Idiotype Expressed by Their Tumors," *N. Engl. J. Med.*, 1992, 327(17):1209-1215.

Marks et al., "By-passing Immunization Human Antibodies from V-gene Libraries Displayed on Phage," *J. Mol. Biol.*, 1991, 222(3):581-597.

Marlin and Springer, "Purified Intercellular Adhesion Molecule-1 (ICAM-1) Is a Ligand for Lymphocyte Function-Associated Antigen 1 (LFA-1)," *Cell*, 1987, 51:813-819.

Marquardt, "An Algorithm for Least-Square Estimation of Nonlinear Parameters," *J. Soc. Indust. Appl. Math.*, 1963, 11(9):431-441.

Maruo et al., "ICAM-1 Expression and the Soluble ICAM-1 Level for Evaluating the Metastatic Potential of Gastric Cancer," *Int. J. Cancer*, 2002, 100:486-490.

Menezes et al., "Establishment and characterization of an Epstein-Barr Virus (EBV)-Negative Lymphoblastoid B Cell Line (BJA-B) from an Exceptional, EBV-Genome-Negative African Burkitt's Lymphoma," *Biomedicine*, 1975, 22:276-284.

Miller et al., "Treatment of B-Cell Lymphoma with Monoclonal Anti-Idiotype Antibody," *N. Engl. J. Med.*, 1982, 306(9):517-522.

Nagy and Mooney, "A novel, alternative pathway of apoptosis triggered through class II major histocompatibility complex molecules," *J. Mol. Med.*, 2003, 81:757-765.

Nagy et al., "Fully human, HLA-DR-specific monoclonal antibodies efficiently induce programmed death of malignant lymphoid cells," *Nat. Med.*, 2002, 8(8):801-807.

Nieda et al., "Dendritic cells rapidly undergo apoptosis in vitro following culture with activated CD4⁺Vα24 natural killer T cells expressing CD40L," *Immunology*, 2001, 102(2):137-145.

Nord et al., "Binding proteins selected from combinatorial libraries of an α-helical bacterial receptor domain," *Nat. Biotechnol.*, 1997, 15(8):772-777.

Norderhaug et al., "Versatile vectors for transient and stable expression of recombinant antibody molecules in mammalian cells," *J. Immunol. Meth.*, 1997, 204:77-87.

Riechmann et al., "Reshaping human antibodies for therapy," *Nature*, 1988, 332:323-327.

Robert et al., "Cutaneous side-effects of kinase inhibitors and blocking antibodies," *Lancet Oncol.*, 2005, 6:491-500.

Roche et al., "Fibrinogen mediates bladder cancer cell migration in an ICAM-1-dependent pathway," *Thromb. Haemost.*, 2003, 89:1089-1097.

Rosenthal, "A Graphic Method for the Determination and Presentation of Binding Parameters in a Complex System," *Anal. Biochem.*, 1967, 20:525-532.

Rosette et al., "Role of ICAM1 in invasion of human breast cancer cells," *Carcinogenesis*, 2005, 26(5):943-950.

Rothlein et al., "Cross-Linking of ICAM-1 Induced Co-Signaling of an Oxidative Burst from Mononuclear Leukocytes," *J. Immunol.*, 1994, 152:2488-2495.

Saltman et al., "Characterization of a New Non-Hodgkin's Lymphoma Cell Line (NCEB-1) With a Chromosomal (11:14) Translocation [t(11:14)(q13;q32)]," *Blood*, 1988, 72(6):2026-2030.

Smallshaw et al, "The generation and anti-myeloma activity of a chimeric anti-CD54 antibody, cUV3," *J. Immunother.*, 2004, 27(6):419-424.

Smith and Thomas, "Cellular expression of lymphocyte6 function associated antigens and the intercellular adhesion molecule-1 in normal tissue," *J. Clin. Pathol.*, 1990, 43:893-900.

Soderlind et al., "Recombining germline-derived CDR sequences for creating diverse single-framework antibody libraries," *Nat. Biotechnol.*, 2000, 18(8):852-856.

Suárez et al., "Human monoclonal antibodies produced in transgenic BABκ,λmice recognizing idiotypic immunoglobulins of human lymphoma cells," *Mol. Immunol.*, 2004, 41:519-526.

Sun et al., "Invasion and metastasis of liver cancer: expression of intercellular adhesion molecule 1," *J. Cancer Res. Clin. Oncol.*, 1999, 125:28-34.

Terry et al., "Localization of the rubella E1 epitopes," *Arch. Virol.*, 1988, 98:189-197.

Uyttenhove et al., "Escape of mouse mastocytoma P815 after nearly complete rejection is due to antigen-loss variants rather than immunosuppression," *J. Exp. Med.*, 1983, 157:1040-1052.

Vidovic and Toral, "Selective apoptosis of neoplastic cells by the HLA-DR-specific monoclonal antibody," *Cancer Letters*, 1998, 128:127-135.

Vyth-Dreese et al., "Functional Expression of Adhesion Receptors and Costimulatory Molecules by Fresh and Immortalized B-Cell Non-Hodgkin's Lymphoma Cells," *Blood*, 1995, 85(10):2802-2812.

Wang et al., "Effect of an anti-cd54 (ICAM-1) monoclonal antibody (UV3) on the growth of human uveal melanoma cells transplanted heterotopically and orthotopically in SCID mice," *Int. J. Cancer*, 2006, 118(4):932-941.

Weiner and Kaminski, "Idiotype Variants Emerging After Anti-Idiotype Monoclonal Antibody Therapy of a Murine B Cell Lymphoma," *J. Immunol.*, 1989, 142:343-351.

Weiner and Carter, "Tunable antibodies," *Nat. Biotechnol.*, 2005, 23(5):556-557.

Weng et al., "Generating addressable protein-microarrays with PROfusion covalent mRNA-protein fusion technology," *Proteomics*, 2002, 2:48-57.

Yoshida et al., "Activated monocytes induce human retinal pigment epithelial cell apoptosis through caspase-3 activation," *Laboratory Investigation*, 2003, 83(8):1117-1129.

Zen et al., "Monocyte-derived macrophages prime peripheral T cells to undergo apoptosis by cell-cell contact via ICAM-1/LFA-1-dependent mechanism," *Immunobiology*, 1996, 195(3):323-333.

Miele et al., "Enhanced Metastatic Ability of TNF-$\alpha$-Treated Malignant Melanoma Cells Is Reduced by Intercellular Adhesion Molecular-1 (ICAM-1, CD54) Antisense Oligonucleotides," *Exp. Cell Res.*, 1994, 214:231-241.

Kroemer, et al., "Classification of cell death: recommendations of the Nomenclature Committee on Cell Death 2009," Cell Death and Differentiation (2009) 16, 3-11.

\* cited by examiner

Figure 2:
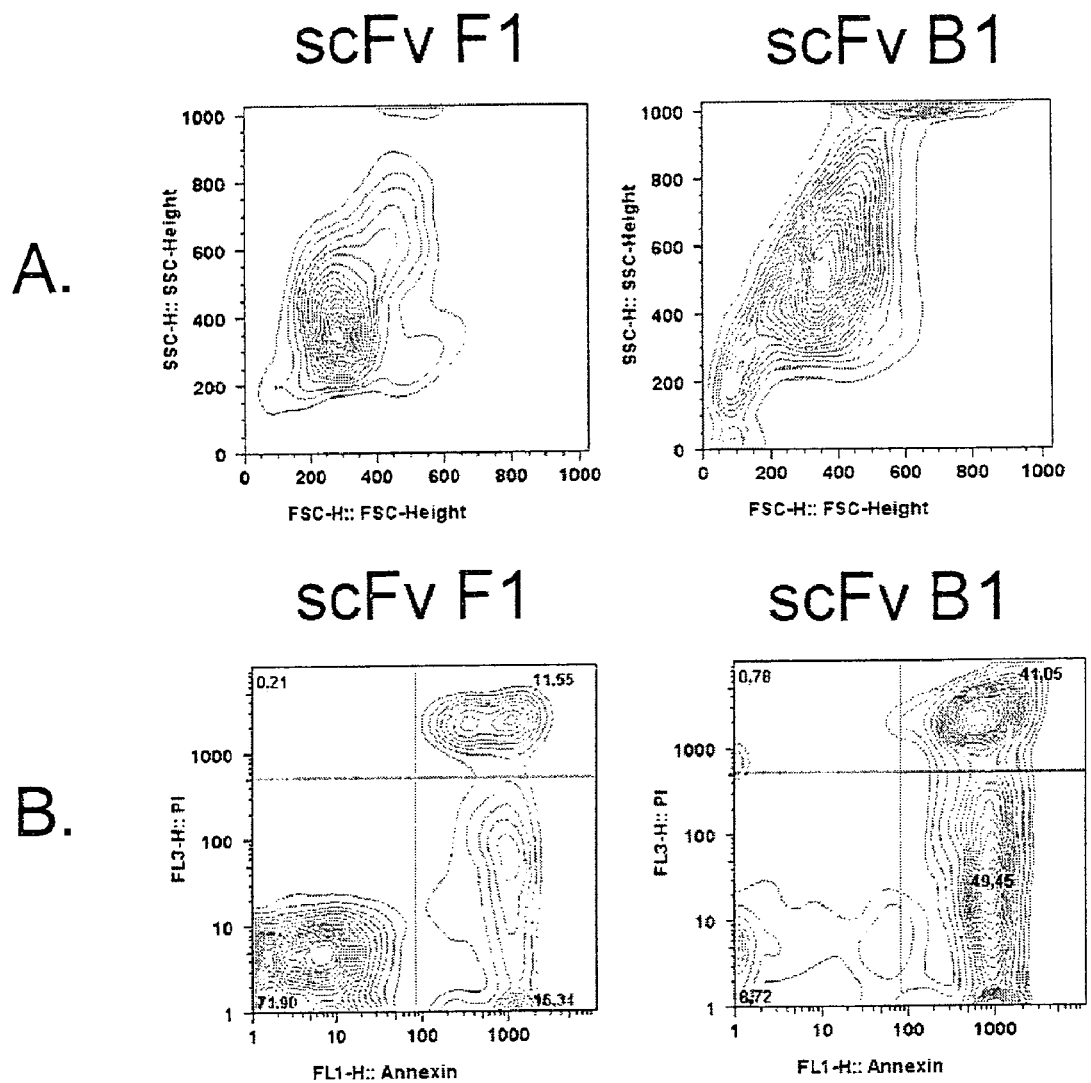

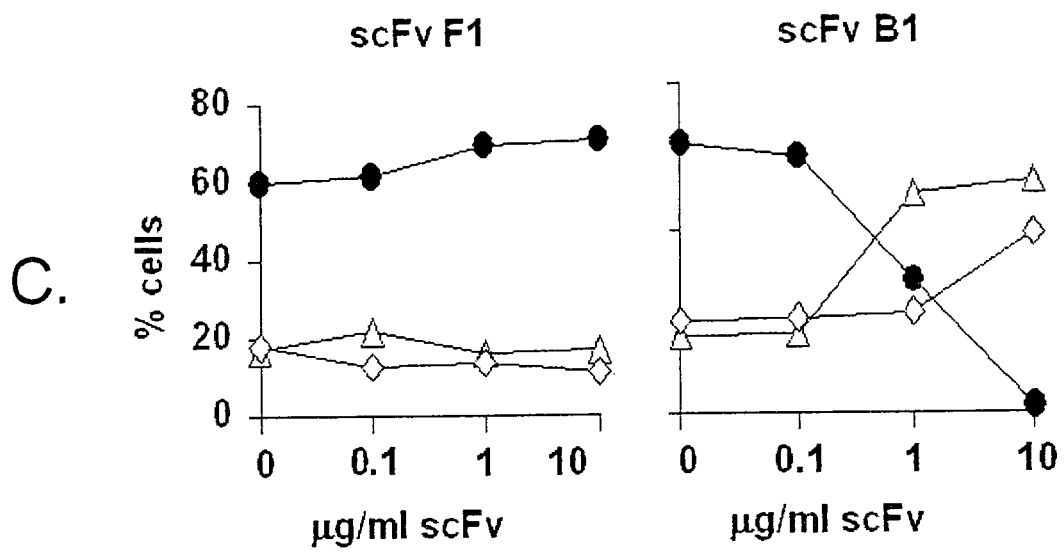
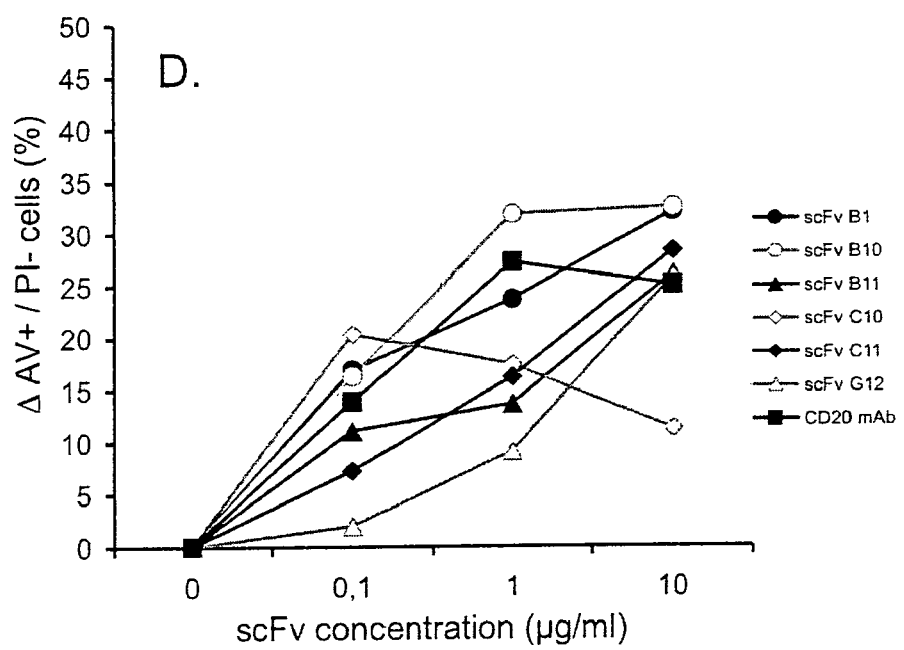
*Figure 2 (con't)*

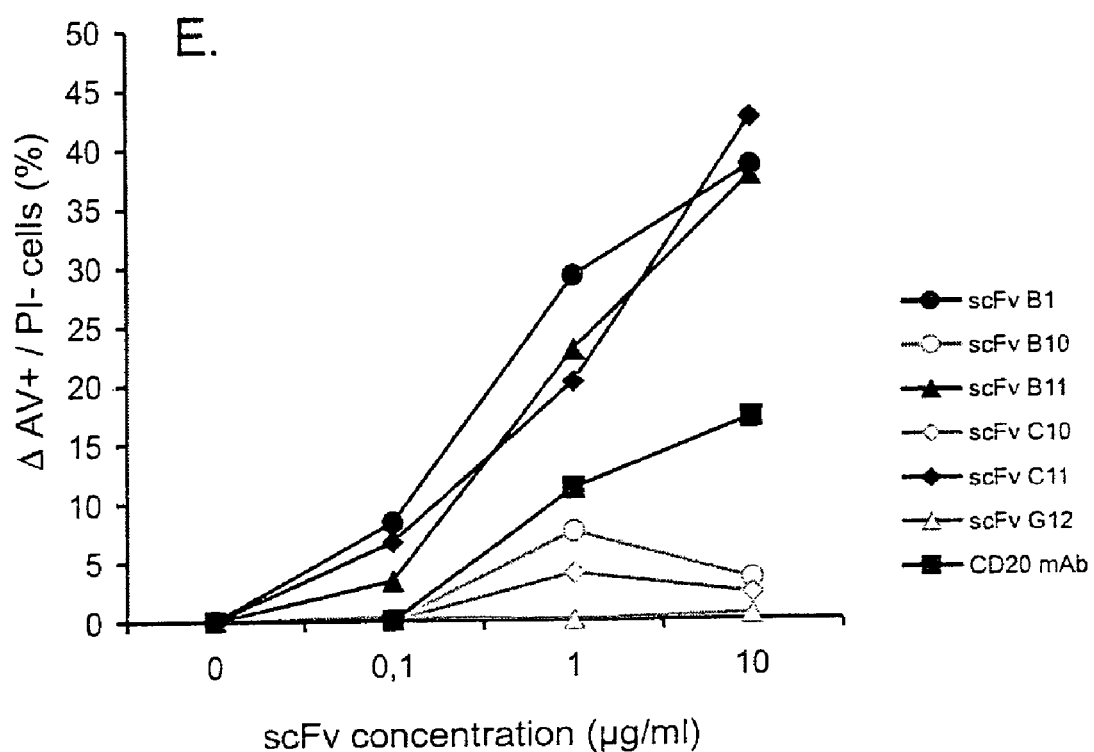
Figure 2 (con't)

A.

B.

Figure 4:
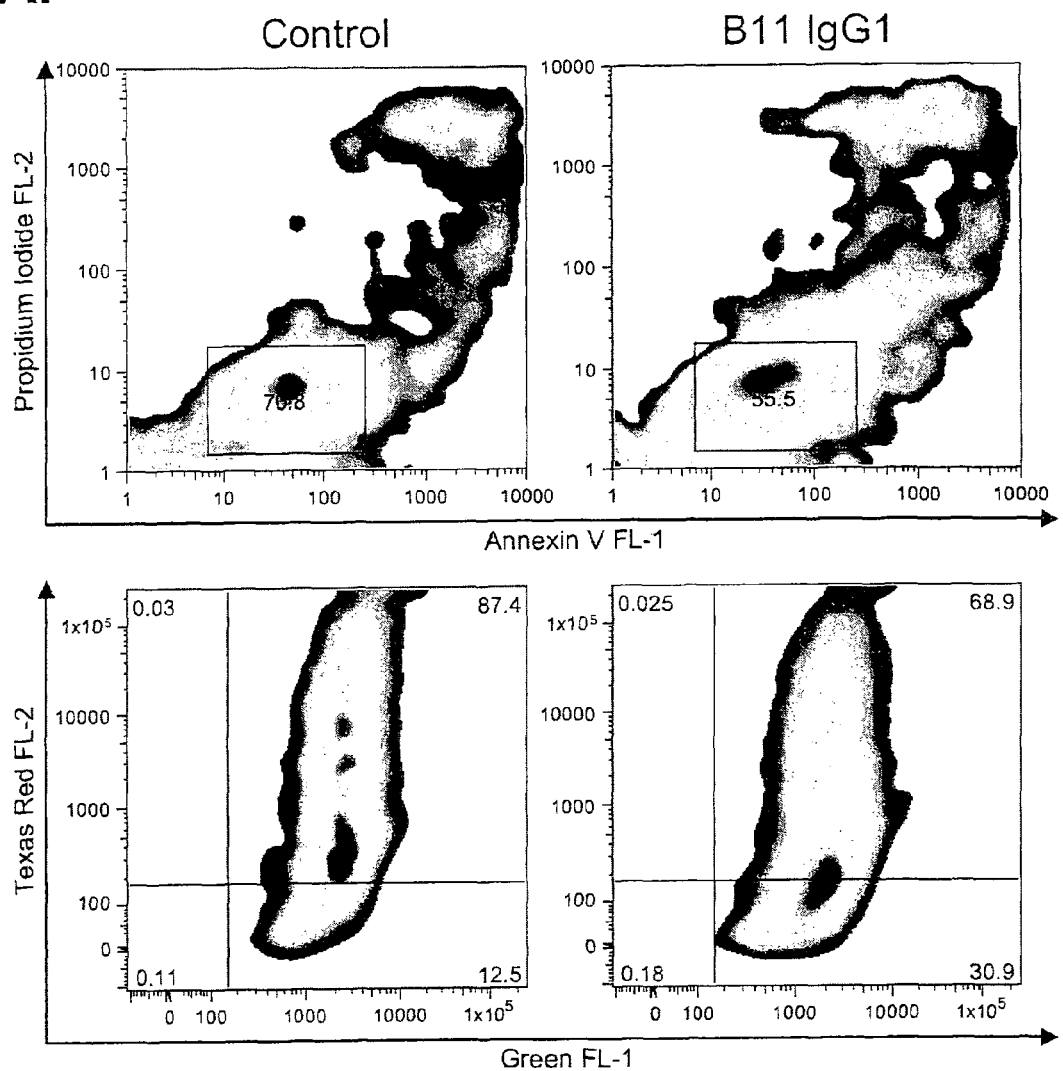

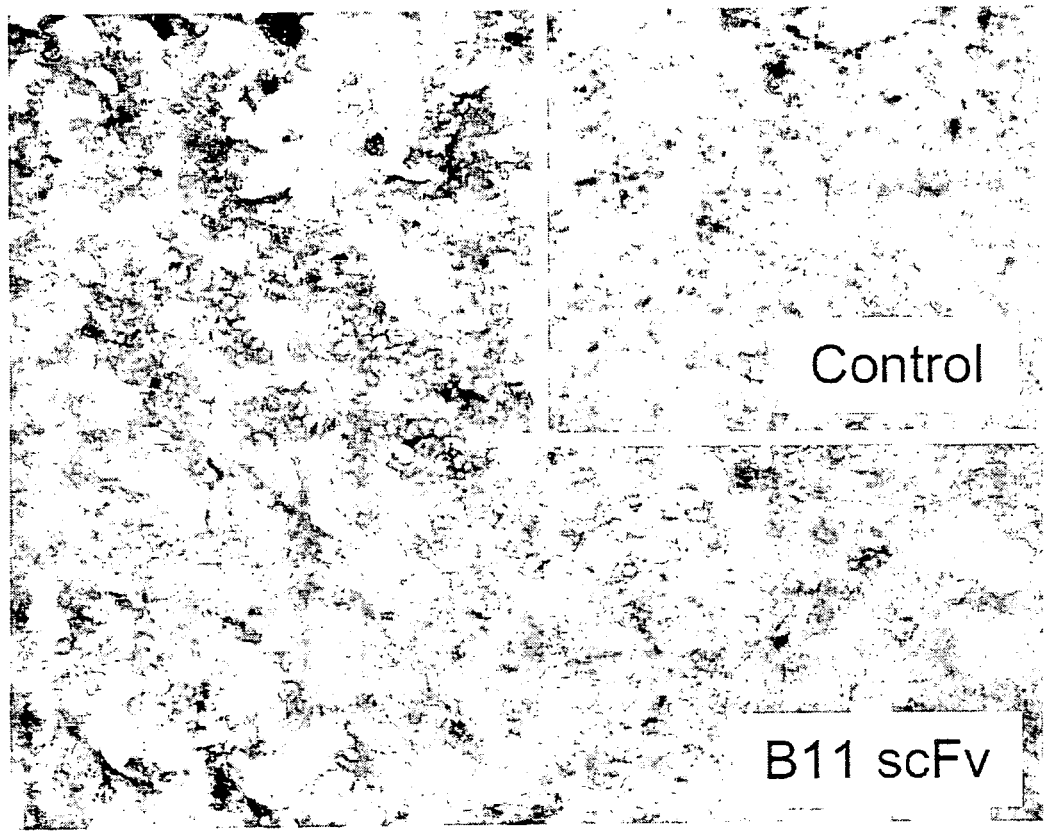
*Figure 4 (con't)*

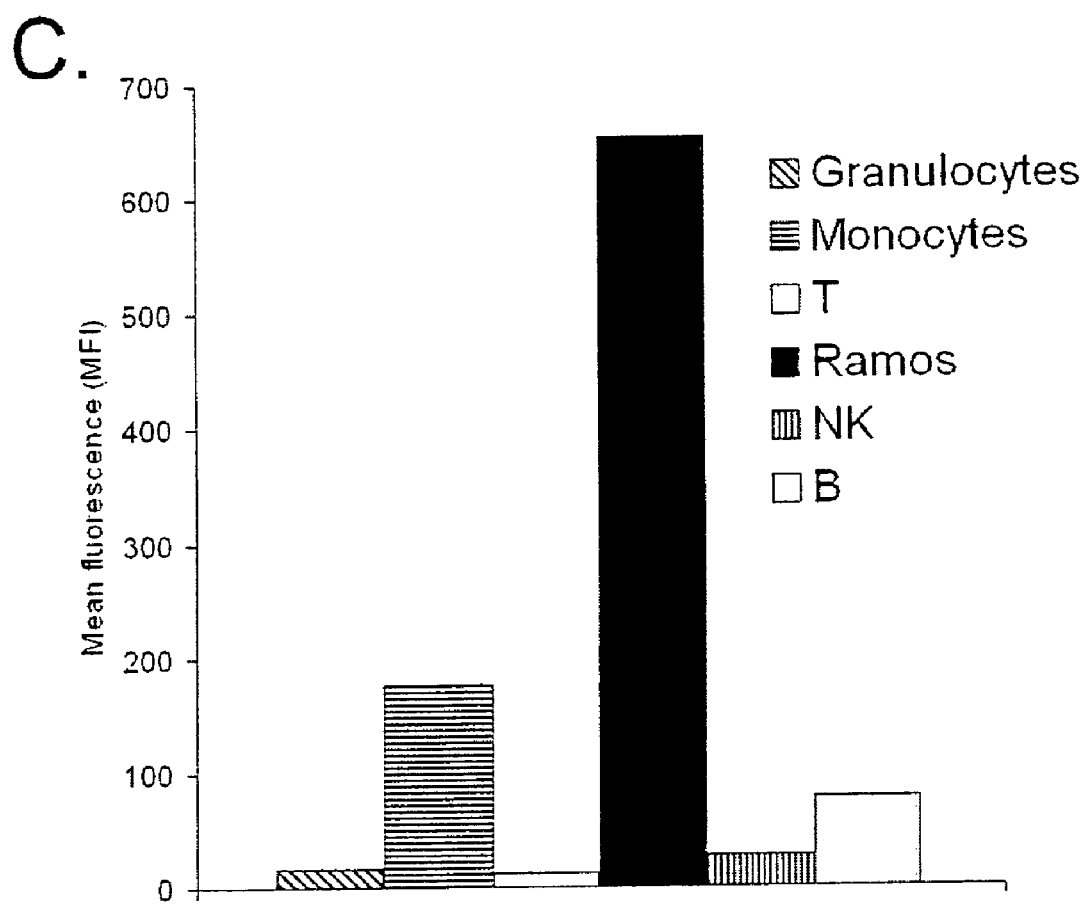
*Figure 4 (con't)*

A.

B.

Figure 7:
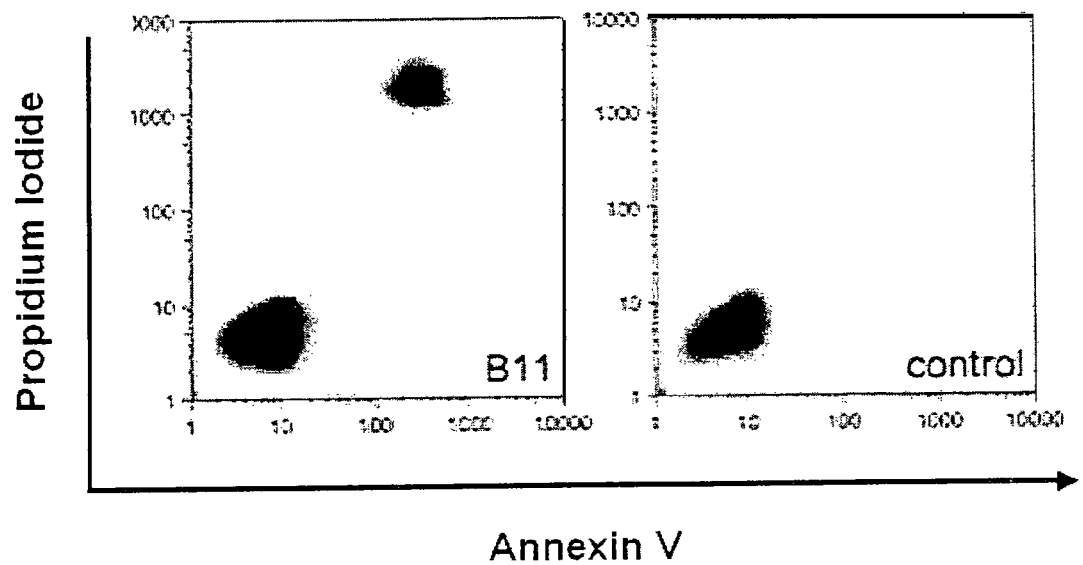
Figure 7:
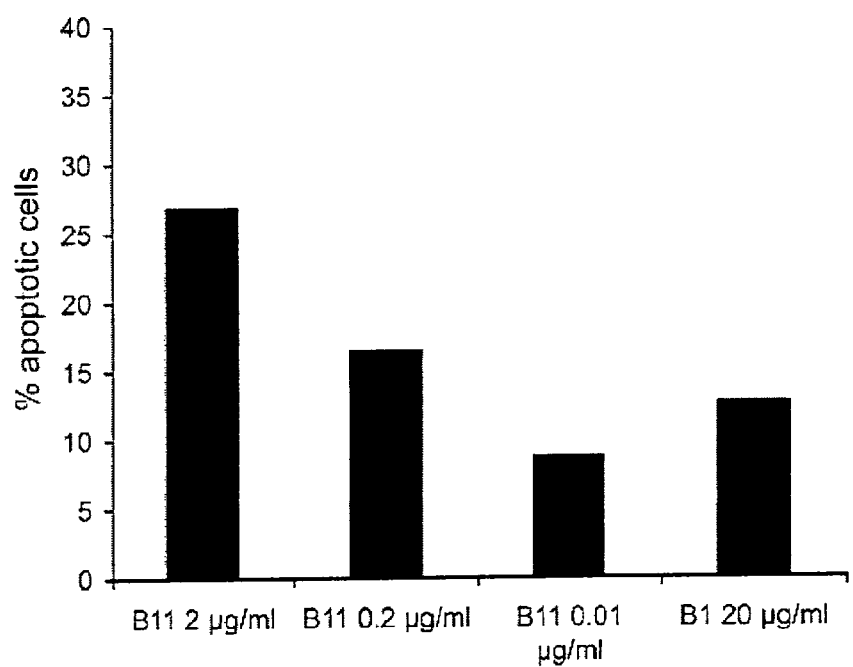

C.
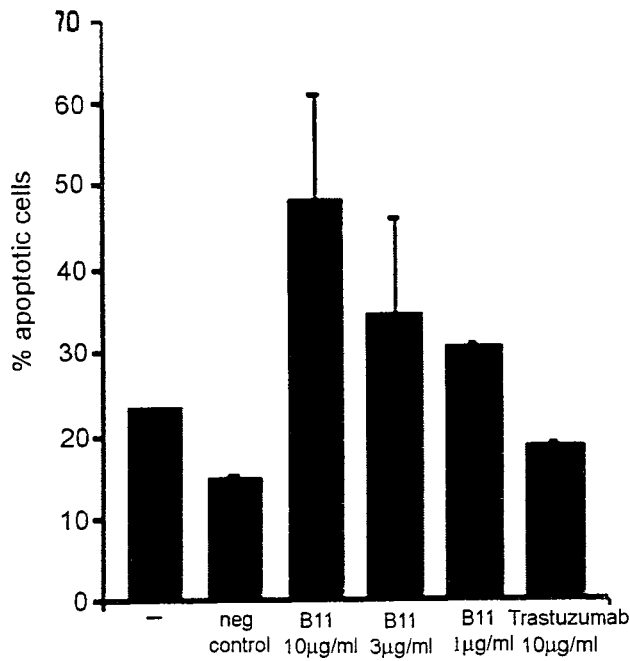
D.
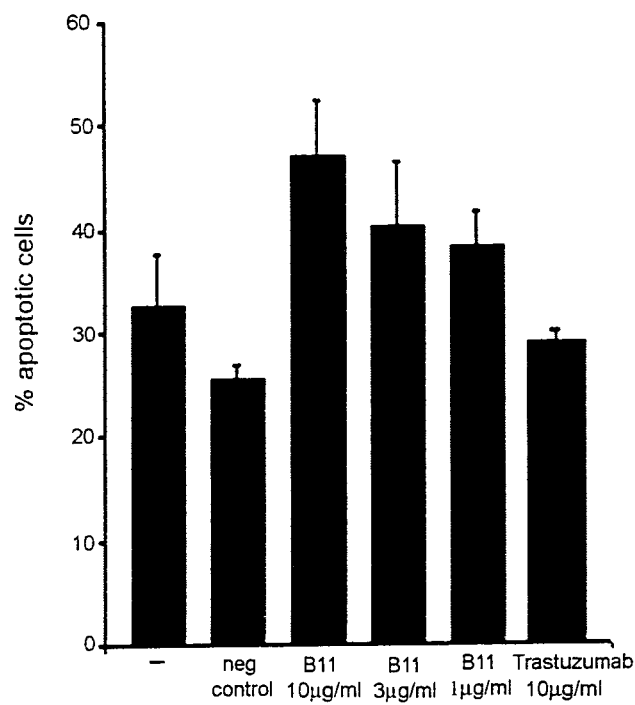
*Figure 7 (con't)*

B1-VH

Nucleotide sequence:

GAGGTGCAGCTGTTGGAGTCTGGGGGAGGCTTGGTACAGCCTGGGGGGTCCCT
GAGACTCTCCTGTGCAGCCTCTGGATTCACCTTTAGCAGCTATGCCATGAGCT
GGGTCCGCCAGGCTCCAGGGAAGGGGCTGGAGTGGGTCTCAGCTATTAGTGGT
AGTGGTGGTAGCACATACTACGCAGACTCCGTGAAGGGCCGGTTCACCATCTC
CAGAGACAATTCCAAGAACACGCTGTATCTGCAAATGAACAGCCTGAGAGCCG
AGGACACTGCCGTGTATTACTGTGCGAGAGATGGGCTACTACCCCTTGACTAC
TGGGGCCAGGGTACACTGGTCACCGTGAGCTCA

Amino acid sequence:

EVQLLESGGGLVQPGGSLRLSCAASGFTFSSYAMSWVRQAPGKGLEWVSAISG
SGGSTYYADSVKGRFTISRDNSKNTLYLQMNSLRAEDTAVYYCARDGLLPLDY
WGQGTLVTVSS

*Figure 9*

B1-VL

Nucleotide sequence:

CAGTCTGTGCTGACTCAGCCACCCTCAGCGTCTGGGACCCCCGGGCAGAGGGT
CACCATCTCTTGTTCTGGAGGCAGCTCCAACATCGGAGGGAATGCTGTAAATT
GGTATCAGCAGCTCCCAGGAACGGCCCCCAAACTCCTCATCTATGAAAATAAT
AAGCGACCCTCAGGGGTCCCTGACCGATTCTCTGGCTCCAAGTCTGGCACCTC
AGCCTCCCTGGCCATCAGTGGGCTCCGGTCCGAGGATGAGGCTGATTATTACT
GCAGCTCATATGCGGTCAGCAACAATTTCGAGGTGCTATTCGGCGGAGGAACC
AAGCTGACGGTCCTAGGT

Amino acid sequence:

QSVLTQPPSASGTPGQRVTISCSGGSSNIGGNAVNWYQQLPGTAPKLLIYENN
KRPSGVPDRFSGSKSGTSASLAISGLRSEDEADYYCSSYAVSNNFEVLFGGGT
KLTVLG

*Figure 9 (con't)*

B11-VH

Nucleotide sequence:

GAGGTGCAGCTGTTGGAGTCTGGGGGAGGCTTGGTACAGCCTGGGGGGTCCCT
GAGACTCTCCTGTGCAGCCTCTGGATTCACCTTCAGTAACGCCTGGATGAGCT
GGGTCCGCCAGGCTCCAGGGAAGGGGCTGGAGTGGGTGGCATTTATATGGTAT
GATGGAAGTAATAAATACTATGCAGACTCCGTGAAGGGCCGATTCACCATCTC
CAGAGACAATTCCAAGAACACGCTGTATCTGCAAATGAACAGCCTGAGAGCCG
AGGACACTGCCGTGTATTACTGTGCGAGATACAGTGGCTGGTACTTTGACTAC
TGGGGCCAAGGTACACTGGTCACCGTGAGCTCA

Amino acid sequence:

EVQLLESGGGLVQPGGSLRLSCAASGFTFSNAWMSWVRQAPGKGLEWVAFIWY
DGSNKYYADSVKGRFTISRDNSKNTLYLQMNSLRAEDTAVYYCARYSGWYFDY
WGQGTLVTVSS

*Figure 10*

B11-VL

Nucleotide sequence:

CAGTCTGTGCTGACTCAGCCACCCTCAGCGTCTGGGACCCCCGGGCAGAGGGT
CACCATCTCCTGCACTGGGAGCAGCTCCAACATCGGGGCAGGTTATGATGTAC
ACTGGTATCAGCAGCTCCCAGGAACGGCCCCCAAACTCCTCATCTATGATAAC
AACAATCGGCCCTCAGGGGTCCCTGACCGATTCTCTGGCTCCAAGTCTGGCAC
CTCAGCCTCCCTGGCCATCAGTGGGCTCCGGTCCGAGGATGAGGCTGATTATT
ACTGCCAGTCCTATGACAGCAGCCTCAGTGCTTGGCTGTTCGGCGGAGGAACC
AAGCTGACGGTCCTAGGT

Amino acid sequence:

QSVLTQPPSASGTPGQRVTISCTGSSSNIGAGYDVHWYQQLPGTAPKLLIYDN
NNRPSGVPDRFSGSKSGTSASLAISGLRSEDEADYYCQSYDSSLSAWLFGGGT
KLTVLG

*Figure 10 (con't)*

C11-VH

Nucleotide sequence:

GAGGTGCAGCTGTTGGAGTCTGGGGGAGGCTTGGTACAGCCTGGGGGGTCCCT
GAGACTCTCCTGTGCAGCCTCTGGATTCACCTTCGGCAGTTATGAAATGAACT
GGGTCCGCCAGGCTCCAGGGAAGGGGCTGGAGTGGGTCTCAGTTATTTATAGC
GGTGGTAGCACATACTACGCAGACTCCGTGGAAGGCCGATTCACCATCTCCAG
AGACAATTCCAAGAACACGCTGTATCTGCAAATGAACAGCCTGAGAGCCGAGG
ACACTGCCGTGTATTACTGTGCGAGAGATACAAACCCGTACTACTACTACGGT
ATGGACGTCTGGGGCCAAGGTACACTGGTCACCGTGAGCTCA

Amino acid sequence:

EVQLLESGGGLVQPGGSLRLSCAASGFTFGSYEMNWVRQAPGKGLEWVSVIYS
GGSTYYADSVEGRFTISRDNSKNTLYLQMNSLRAEDTAVYYCARDTNPYYYYG
MDVWGQGTLVTVSS

*Figure 11*

C11-VL

Nucleotide sequence:

CAGTCTGTGCTGACTCAGCCACCCTCAGCGTCTGGGACCCCCGGGCAGAGGGT
CACCATCTCCTGTTCTGGAAGCAGCTCCAACATCGGAAATAATGCTGTAAACT
GGTATCAGCAGCTCCCAGGAACGGCCCCCAAACTCCTCATCTATAGGAATAAT
CAGCGGCCCTCAGGGGTCCCTGACCGATTCTCTGGCTCCAAGTCTGGCACCTC
AGCCTCCCTGGCCATCAGTGGGCTCCGGTCCGAGGATGAGGCTGATTATTACT
GCCAGTCCTATGACAGCAGCCTGAATGGTCAAGTATTCGGCGGAGGAACCAAG
CTGACAGTCCTAGGT

Amino acid sequence:

QSVLTQPPSASGTPGQRVTISCSGSSSNIGNNAVNWYQQLPGTAPKLLIYRNN
QRPSGVPDRFSGSKSGTSASLAISGLRSEDEADYYCQSYDSSLNGQVFGGGTK
LTVLG

*Figure 11 (con't)*

US 7,943,744 B2

ICAM-1 BINDING ANTIBODIES

CROSS-REFERENCE TO RELATED APPLICATIONS

This application is a National Stage application under 35 U.S.C. §371 and claims benefit under 35 U.S.C. §119(a) of International Application No. PCT/EP2006/012065 having an International Filing Date of Dec. 8, 2006, which claims the benefit of priority of GB 0525214.3 having a filing date of Dec. 12, 2005, all of which are incorporated herein in their entirety.

The invention relates to molecules involved in apoptosis induction, methods and pharmaceutical compositions for apoptosis induction and uses thereof.

Antibodies have recently become the protein therapeutics of choice for targeting cancer but also for treating other indications (Brekke et al. Nat Rev Drug Discov 2003; 2:52-62). The advent of antibody engineering has provided the tools to generate human antibodies from synthetic phage libraries, displaying decreased immunogenicity and enhanced specificity and affinity due to their human nature and greater diversity (Weiner et al. Nat Biotechnol 2005; 23:556-7). Naïve libraries are particularly attractive, as they may be used for isolation of antibodies for any specificity, including self-antigens (Griffiths et al. Embo J 1993; 12:725-34), independent of immunizations and reconstruction of new libraries. Cell surface receptors constitute by far the most successful group of antigens targeted by contemporary therapeutic drugs, including small molecule inhibitors and antibodies. Of particular interest are cell surface receptors that are uniquely expressed or that display an increased expression level on a target cell and are additionally capable of relaying death or survival signals to the cell. Such differentially expressed receptors with intrinsic signalling properties enable antibody-based targeting of microbial infected, transformed, or otherwise malfunctioning cells.

For treatment of tumours, antibodies that have the ability to induce apoptosis in a target tumour cell whilst sparing normal tissue are of particular interest. Several such antibodies are in use, have been registered with the US Food and Drug Administration (FDA) and provide alternatives to conventional cancer treatments e.g. for lymphoma (rituximab targeting CD20) or for breast cancer (trastuzumab or cetuximab targeting Her-2 and EGFR respectively).

There are also other antibodies with apoptosis inducing effects currently in clinical development. However, even if these antibodies demonstrate beneficial effects in patients or in animal tests an unmet clinical need still exists.

Anti-idiotypic immunoglobulin targeting of B cell tumours was the first monoclonal antibody therapy conducted in man (Miller et al. N Engl J Med 1982; 306:517-22.). Destruction of tumour cells by such means of passive antibody administration (Riechmann et al. Nature 1988; 332:323-7.), or active vaccination with the patients own tumour immunoglobulin protein (Kwak et al. N Engl J Med 1992; 327:1209-15.), has since been demonstrated to confer tumour regression or tumour dormancy in patients with different kinds of B cell malignancies. A more recent report describes the generation of fully human anti-idiotype antibodies using transgenic mice deficient in mouse antibody production and expressing selected human antibody chain loci (Suarez et al. Mol Immunol 2004; 41:519-26.).

In the present invention a competition biopanning method has been used, where target cell antigen in the form of whole cells, and excess subtractor cell antigen in the form of membrane vesicles, are exposed at the same time to the naïve n-CoDeR® antibody phage library (WO 2004/023140; Soderlind et al. Nat Biotechnol 2000; 18:852-6.), to retrieve and subsequently test antibody fragments with excellent selectivity for B lymphoma target cells. Furthermore, functionality in the selected binding molecules was demonstrated by the ability of the antibodies tested to induce apoptosis in target but not in non-target cells.

Antibody specificities identified include HLA-DR/DP (the B1 antibody of the invention) and surface IgM (the C11 antibody of the invention), as well as ICAM-1 (the B11 antibody of the invention), an adhesion molecule not previously associated with apoptosis induction. Isolated antibodies had affinities in the sub-nanomolar to nanomolar range, directly making them possible choices for targeted antibody therapy.

SUMMARY OF THE INVENTION

In a first aspect of the invention there is provided a method of inducing apoptosis in a target cell comprising the steps:
a. providing one or more target cells displaying the cell surface antigen, ICAM-1;
b. providing one or more binding molecules which selectively binds to cell surface ICAM-1 and, on binding ICAM-1, induces apoptosis of the target cell;
c. exposing the target cells of (a) to the binding molecules of (b) to induce apoptosis in the target cells.

Preferably the binding molecule is an antibody molecule.

In a second aspect of the invention there is provided a method of inducing apoptosis in a target cell comprising the steps:
a. providing one or more target cells displaying the cell surface antigen, HLA-DR/DP and/or surface IgM;
b. providing one or more antibody molecules which selectively binds to cell surface HLA-DR/DP and/or surface IgM and, on binding HLA-DR/DP and/or surface IgM, inducing apoptosis of the target cell;
c. exposing the target cells of (a) to the antibody molecules of (b) to induce apoptosis in the target cells.

In a third aspect of the invention there is provided a binding molecule which selectively binds to cell surface ICAM-1 and, on binding ICAM-1, induces apoptosis of the target cell. Alternatively the binding molecule is an antibody molecule that selectively binds to cell surface HLA-DR/DP and/or surface IgM.

ICAM-I is also designated CD54, but for the purpose of this application ICAM-1 will be used.

Binding molecules may be derived from antibodies and based on the antibody scaffold [Clackson T et al., Nature. 1991 Aug. 15; 352(6336):624-8, Marks J D et al., J Mol. Biol. 1991 Dec. 5; 222(3):581-97] that has been used extensively in many libraries, but binding molecules may also be derived form other molecular scaffolds such as the fibronectin scaffold [Weng S et al., Proteomics. 2002 January; 2(1):48-57] and the protein A scaffold [Nord K, et al., Nat Biotechnol 1997 August; 15(8):772-7, Hogbom M et al., Proc Natl Acad Sci USA. 2003 Mar. 18; 100(6):3191-6]. Each of these scaffolds may have their advantages depending on application, and the antibody scaffold, as one example, may be used advantageously for creating variability indistinguishable from natural variability.

The basic structure of the antibody, the most commonly used scaffold, is very well understood. In principle, a framework structure comprising beta strands ordered into two sheets present a set of variable loops, the so called Complementary Determining Regions (CDRs) that have the capacity to bind to antigen molecules. Although antibodies may vary in the scaffold structure the most extensive variability is seen in the CDRs. The great variability in-between antibodies, is the basis for their ability to interact, in a specific manner, with in principle all types of molecular structures. Due to this capacity, antibodies have been used extensively for generation of specific binders with applicability within research, diagnosis/prognosis of disease and as therapeutic agents specific for defined target structures [Borrebaeck C A and Carlsson R, Curr Opin Pharmacol. 2001 August; 1(4):404-8].

Other, non-antibody binding molecules useful in this invention are those having scaffold structures with a high degree of stability yet allowing variability to be introduced at certain positions. An example of another binding molecule is a fibronectin domain and a 58 amino acids large protein A domain which tolerate variability. There are also other molecular folds that allow some degree of variation. Such examples include major histocompatibility complex (MHC) class I and II molecules and recently a novel class of molecules the so called defensins have been identified to be similar in basic structure while still harbouring extensive sequence variability in-between the gene family members indicating that they are suitable as scaffolds for harbouring molecular diversity. In addition, natural ligand(s) e.g. LFA-1 in the case of ICAM-1 as a target molecule, or recombinant variants of them, may constitute specific binding molecules able to induce apoptosis in target cells.

Furthermore, the binding molecule may be any molecule selectively binding cell surface ICAM-1 of a target cell and, on binding, inducing apoptosis of the target cell.

The binding molecule is preferably an antibody molecule.

In one embodiment the cell surface antigen is ICAM-1.

The present screening retrieved an antibody (B11) specific for ICAM-1—a receptor not previously associated with apoptosis and not attributed intrinsic negative signalling properties in cells.

The identification of ICAM-1 as an apoptosis-inducing molecule was a direct result of the screening being designed to isolate specificities for all surface receptors differentially expressed between target and non-target cells, irrespective of and without prior knowledge of their respective identity. ICAM-1-induced cell death has been verified as an active apoptotic process that involved mitochondrial membrane depolarization. Mitochondrial membrane depolarization has been previously described for both caspase dependent and caspase independent apoptosis (Nagy et al. J Mol Med 2003; 81:757-65.).

The present findings further show that the epitope bound by the B11 antibody is expressed in B lymphoma tissue of different origin, and is up regulated in certain B lymphoma cells compared to resting peripheral blood leukocytes. Importantly, in addition to B lymphoma cells also carcinoma cells expressing ICAM-1 underwent apoptosis when subjected to the ICAM-1 specific B11 antibody in vitro (see Example 6).

Previous studies have demonstrated restricted expression of ICAM-1 on normal human tissues (Smith et al. J Clin Pathol 1990; 43:893-900.). ICAM-1 is involved in cell to cell adhesion and plays an important role in immune responses and inflammation through binding to its receptor LFA-1. Antibodies directed to ICAM-1 have been used to interfere with pathological immune responses and inflammation. In vivo administration of a murine anti-ICAM-11 mAb in cymologous monkeys (Cosimi et al. J Immunol 1990; 144: 4604-12.), or use in clinical trials in human patients with rheumatoid arthritis or patients receiving kidney transplants has also revealed no overt toxicity (Kavanaugh et al. Arthritis Rheum 1994; 37:992-9; Haug et al. Transplantation 1993; 55:766-72.).

The novel finding that ICAM-1 targeting can lead to apoptosis demonstrates the possibility to use ICAM-1 specific binding molecules, such as antibodies for treatment of cancers of different origins provided that they express the antigen.

Based on their expression of ICAM-1 cancer types that may potentially be treated with an apoptosis inducing anti-ICAM-1 antibody such as B11 include: B lymphoma, myeloma (Huang et al. (1993) Hybridoma 12 p 661-75; Huang et al., (1995) Cancer Res 55 p 610-6; Smallshaw et al., (2004) J Immunother 27 p 419-24), gastric cancer (Maruo et al., (2002) Int J Cancer 100 p 486-90), breast cancer (Rosette et al., (2005) Carcinogenesis 26 p 943-50), liver cancer (Sun et al., (1999) J Cancer Res Clin Oncol 125 p 28-34), lung cancer (Grothey et al., (1998) Br J Cancer 77 p 801-7), melanoma (Wang et al., (2005) Int J Cancer 27 p 419-24), bladder cancer (Roche et al., (2003) Thromb Haemost 89 1089-97) and prostate cancer (Aalinkeel et al., (2004) Cancer Res 64 p 5311-21). Expression of ICAM-1 has also been identified in tumour metastasis as demonstrated by (Maruo et al., 2002), (Rosette et al., 2005), (Sun et al., 1999), (Grothey et al., 1998), (Aalinkeel et al. 2004) pointing to the possibility to intervene in metastasis processes using an ICAM-1 specific antibody.

In a further embodiment the cell surface antigen is HLA-DR/DP.

HLA-DR/DP is normally present on, for example, B cells and can be found up-regulated on B lymphoma cells.

To date, three different HLA-DR specific monoclonal antibodies have entered clinical phase trials. The most recent addition of which is the fully human IgG$_4$ ID09C3, which was isolated from a similarly sized naïve phage library compared to n-CoDeR®, but using solid phase panning on purified antigen (Nagy et al. Nat Med 2002; 8:801-7.).

In the present invention, a novel human antibody (B1) directed against HLA-DR/DP that rapidly and with high potency induces apoptosis in a multitude of B-lymphoma cell lines has been identified thereby demonstrating HLA-DR/DP is linked to the induction of apoptosis in a target cell.

Figure 8:
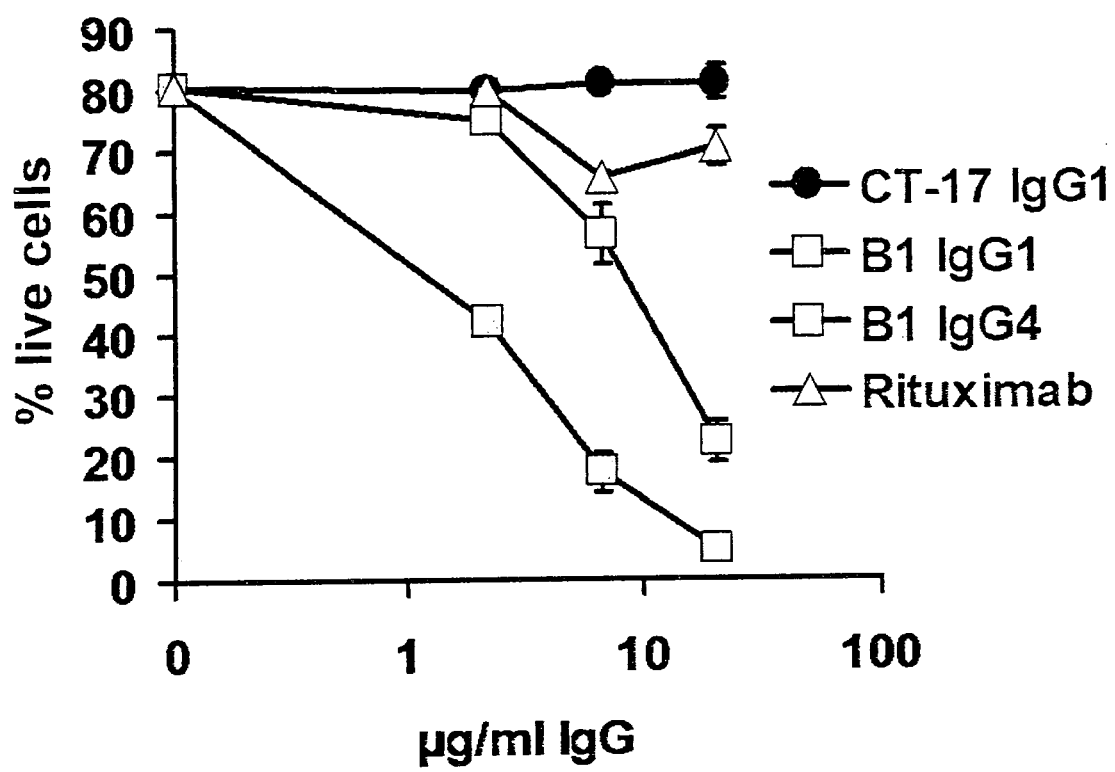

The B1 antibody bound a multitude of B lymphoma cell lines of different origin (see Example 1 and Table 1) and was shown to induce apoptosis in HLA-DR/DP antigen expressing cells. Furthermore, the B1 antibody showed a higher potency than Rituximab when tested on the Raji B lymphoma cell line. This was particularly evident, when the IgG$_4$ format of the B1 antibody was used (FIG. 8).

From the data obtained, this antibody has suitable characteristics for treatment of HLA-DR/DP expressing B lymphoma cells. In addition, similar to the targeting of Rheumatoid Arthritis and SLE by Rituximab, the B1 antibody may prove efficacious in eliminating activated B cells in disorders where HLA-DR/DP expressing B cells are detrimental.

In a yet further embodiment the cell surface antigen is surface IgM.

IgM in its free form exists as a large pentameric structure, whose higher molecular weight tends to confine it within blood vessels.

Monomeric IgM can be found on the cell walls of B lymphocytes and functions as an antibody receptor for antigen recognition.

The C11 antibody of the invention, upon binding to surface IgM, expressed on B lymphoma cells, induces apoptosis in a rapid and efficient manner (see Example 1 and Table 1). In contrast to the idiotype specific anti-IgM antibodies previously used in the clinic for treatment of B lymphoma the C11 antibody bind to a non-polymorphic epitope expressed on B cells from different donors and is thus suitable for treatment of patients suffering from B lymphoma irrespective of B lymphoma idiotype.

Notably, the effector molecule e.g. the anti-IgM antibody could also be any type of specific binding molecule that causes apoptosis in IgM expressing cells of different idiotypes.

The kinetics of B1, B11 and C11 IgG induced apoptosis were fast, with maximal efficacy being observed already after 3 hours in some cell lines. Rapid effector function is important for therapeutic efficacy as this minimizes the risk for tumour evasion resulting from e.g. lack of expression of tumour antigen (Uyttenhove et al. J. Exp. Med. 1983; 157: 1040-52; Kennedy et al. Br J Haematol 2002; 119:412-6) or epitope mutation (Weiner et al. J Immunol 1989; 142:343-51; Bai et al. J. Clin. Invest. 2003; 111:1487-96), and potentially limits treatment duration and side-effects (Robert et al. Lancet Oncol 2005; 6:491-500.).

Preferably the target cell is an immune cell or epithelial cell and advantageously that immune cell is a B lymphocyte.

Conveniently the target cell is associated with a disease. Preferably the disease is selected from the group consisting of: cancer; autoimmune diseases including but not restricted to rheumatoid arthritis and SLE, acute and chronic inflammatory disorders, sepsis and infectious disease including but not restricted to HIV.

Advantageously, the disease is a cancer selected from lymphoma (leukaemia, myeloma), gastric cancer, breast cancer, liver cancer, lung cancer, melanoma, bladder cancer, chorioid cancer, pancreatic cancer, colon cancer and prostate cancer.

As defined in the definitions section of this application, the phrase antibody molecule is used for convenience and embraces, amongst other things, antibodies, an antibody fragments, and antibody derivatives.

Conveniently, the antibody molecule is an IgG. The IgG may be any of $IgG_1$, $IgG_2$, $IgG_3$ or $IgG_4$, but preferably any of $IgG_1$ and $IgG_4$. The antibody molecule is preferably humanized or human.

Conveniently, the binding molecule or antibody molecule of the invention has the sequence of any one of variable region sequences of FIGS. 9 to 11 or functionally equivalent homologues thereof.

In one embodiment of the invention the binding molecule or antibody molecule has the variable region sequences of FIG. 9 or functionally equivalent homologues thereof.

In a further embodiment of the invention, the binding molecule or antibody molecule has the variable region sequences of FIG. 10 or functionally equivalent homologues thereof.

In a yet further embodiment of the invention, the binding molecule or antibody molecule has the variable region sequences of FIG. 11 or functionally equivalent homologues thereof.

In a fourth aspect of the invention there is provided a nucleic acid having a nucleotide sequence encoding a binding molecule or an antibody molecule as claimed in any previous claim.

Conveniently the nucleic acid has the nucleotide sequence of any one of FIGS. 9 to 11.

In a fifth aspect of the invention there is provided use of the binding molecule or antibody molecule as defined in the first or second aspect of the invention in the diagnosis and/or treatment and/or prevention of a disease requiring the destruction of a target cell. There is also provided the use of the binding molecule or antibody molecule as defined in the first or second aspect of the invention in the manufacture of a medicament for the treatment and/or prevention of a disease requiring the destruction of a target cell.

In a preferred embodiment the binding molecule is an antibody molecule.

Conveniently, the disease to be treated is selected from the group consisting of: cancer; autoimmune diseases including but not restricted to rheumatoid arthritis and SLE, acute and chronic inflammatory disorders, sepsis and infectious disease including but not restricted to HIV.

Advantageously the disease to be treated is cancer selected from lymphoma (leukaemia, myeloma), gastric cancer, breast cancer, liver cancer, lung cancer, melanoma, bladder cancer, chorioid cancer, pancreatic cancer, colon cancer and prostate cancer.

In one embodiment of the invention the binding molecule or antibody molecule binds specifically to ICAM-1 and/or has the sequence of FIG. 10 and is used in relation to the diseases listed above.

In a further embodiment of the invention the antibody molecule binds specifically to HLA-DR/DP and/or has the sequence of FIG. 9 and is used in relation to the diseases of lymphoma (leukaemia, myeloma), gastric cancer, breast cancer, liver cancer, lung cancer, melanoma, bladder cancer, chorioid cancer, pancreatic cancer, colon cancer and prostate cancer.

In a yet further embodiment of the invention the antibody molecule binds specifically to surface IgM and/or has the sequence of FIG. 11 and is used in relation to the diseases of lymphoma (leukaemia, myeloma), gastric cancer, breast cancer, liver cancer, lung cancer, melanoma, bladder cancer, chorioid cancer, pancreatic cancer, colon cancer and prostate cancer.

In a sixth aspect of the invention there is provided a pharmaceutical composition comprising the binding molecule or antibody molecule of the invention and a pharmaceutically acceptable carrier, excipient or diluent.

In a preferred embodiment the binding molecule is an antibody molecule.

In a seventh aspect of the invention there is provided an in vitro method of inducing apoptosis in a target cell comprising the steps of:
(i) providing one or more target cells;
(ii) providing one or more binding molecules or antibody molecules as defined in the first embodiment of the invention;
(iii) exposing the target cells of (i) to the binding molecules or antibody molecules of (ii) so as to induce apoptosis in the target cells.

In a preferred embodiment the binding molecule is an antibody molecule.

Preferably the target cells provided in step (i) are immune cells or epithelial cells. Advantageously, the immune cells are B lymphocytes.

Conveniently, the target cells are associated with a disease and wherein the disease is selected from the group consisting of: cancer; autoimmune diseases including but not restricted to rheumatoid arthritis and SLE, acute and chronic inflammatory disorders, sepsis and infectious disease including but not restricted to HIV.

Advantageously, the disease is a cancer selected from lymphoma (leukaemia, myeloma), gastric cancer, breast cancer, liver cancer, lung cancer, melanoma, bladder cancer, chorioid cancer, pancreatic cancer, colon cancer and prostate cancer.

Meanings of Terms Used

The term "antibody molecule" shall be taken to refer to any one of an antibody, an antibody fragment, or antibody derivative. It is intended to embrace wildtype antibodies, synthetic antibodies, recombinant antibodies or antibody hybrids, such as, but not limited to, a single-chain modified antibody molecule produced by phage-display of immunoglobulin light and/or heavy chain variable and/or constant regions, or other immunointeractive molecules capable of binding to an antigen in an immunoassay format that is known to those skilled in the art.

The term "antibody fragment" shall be taken to refer to any one of an antibody, an antibody fragment, or antibody derivative. It is intended to embrace wildtype antibodies (i.e. a molecule comprising four polypeptide chains), synthetic antibodies, recombinant antibodies or antibody hybrids, such as, but not limited to, a single-chain modified antibody molecule produced by phage-display of immunoglobulin light and/or heavy chain variable and/or constant regions, or other immunointeractive molecules capable of binding to an antigen in an immunoassay format that is known to those skilled in the art.

The term "antibody derivative" refers to any modified antibody molecule that is capable of binding to an antigen in an immunoassay format that is known to those skilled in the art, such as a fragment of an antibody (e.g. Fab or Fv fragment), or a modified antibody molecule that is modified by the addition of one or more amino acids or other molecules to facilitate coupling the antibodies to another peptide or polypeptide, to a large carrier protein or to a solid support (e.g. the amino acids tyrosine, lysine, glutamic acid, aspartic acid, cysteine and derivatives thereof, $NH_2$-acetyl groups or COOH-terminal amido groups, amongst others).

The term "ScFv molecule" refers to any molecules wherein the $V_H$ and $V_L$ partner domains are linked via a flexible oligopeptide.

The terms "nucleotide sequence" or "nucleic acid" or "polynucleotide" or "oligonucleotide" are used interchangeably and refer to a heteropolymer of nucleotides or the sequence of these nucleotides. These phrases also refer to DNA or RNA of genomic or synthetic origin which may be single-stranded or double-stranded and may represent the sense or the antisense strand, to peptide nucleic acid (PNA) or to any DNA-like or RNA-like material. In the sequences herein A is adenine, C is cytosine, T is thymine, G is guanine and N is A, C, G or T (U). It is contemplated that where the polynucleotide is RNA, the T (thymine) in the sequences provided herein is substituted with U (uracil). Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene.

The terms "polypeptide" or "peptide" or "amino acid sequence" refer to an oligopeptide, peptide, polypeptide or protein sequence or fragment thereof and to naturally occurring or synthetic molecules. A polypeptide "fragment," "portion," or "segment" is a stretch of amino acid residues of at least about 5 amino acids, preferably at least about 7 amino acids, more preferably at least about 9 amino acids and most preferably at least about 17 or more amino acids. To be active, any polypeptide must have sufficient length to display biological and/or immunological activity.

The terms "purified" or "substantially purified" as used herein denotes that the indicated nucleic acid or polypeptide is present in the substantial absence of other biological macromolecules, e.g., polynucleotides, proteins, and the like. In one embodiment, the polynucleotide or polypeptide is purified such that it constitutes at least 95% by weight, more preferably at least 99% by weight, of the indicated biological macromolecules present (but water, buffers, and other small molecules, especially molecules having a molecular weight of less than 1000 daltons, can be present).

The term "isolated" as used herein refers to a nucleic acid or polypeptide separated from at least one other component (e.g., nucleic acid or polypeptide) present with the nucleic acid or polypeptide in its natural source. In one embodiment, the nucleic acid or polypeptide is found in the presence of (if anything) only a solvent, buffer, ion, or other component normally present in a solution of the same. The terms "isolated" and "purified" do not encompass nucleic acids or polypeptides present in their natural source.

The term "recombinant," when used herein to refer to a polypeptide or protein, means that a polypeptide or protein is derived from recombinant (e.g., microbial, insect, or mammalian) expression systems. "Microbial" refers to recombinant polypeptides or proteins made in bacterial or fungal (e.g., yeast) expression systems. As a product, "recombinant microbial" defines a polypeptide or protein essentially free of native endogenous substances and unaccompanied by associated native glycosylation. Polypeptides or proteins expressed in most bacterial cultures, e.g., *Escherichia coli*, will be free of glycosylation modifications; polypeptides or proteins expressed in yeast will have a glycosylation pattern in general different from those expressed in mammalian cells.

The terms "selective binding" and "binding selectivity" indicates that the variable regions of the antibodies of the invention recognise and bind polypeptides of the invention exclusively (i.e., able to distinguish the polypeptide of the invention from other similar polypeptides despite sequence identity, homology, or similarity found in the family of polypeptides), but may also interact with other proteins (for example, *Staphylococcus aureus* protein A or other antibodies in ELISA techniques) through interactions with sequences outside the variable region of the antibodies, and in particular, in the constant region of the molecule. Screening assays to determine binding selectivity of an antibody of the invention are well known and routinely practiced in the art. For a comprehensive discussion of such assays, see Harlow et al. (Eds), Antibodies A Laboratory Manual; Cold Spring Harbor Laboratory; Cold Spring Harbor, N.Y. (1988), Chapter 6. Antibodies that recognise and bind fragments of the polypeptides of the invention are also contemplated, provided that the antibodies are first and foremost selective for, as defined above, full-length polypeptides of the invention. As with antibodies that are selective for full length polypeptides of the invention, antibodies of the invention that recognise fragments are those which can distinguish polypeptides from the same family of polypeptides despite inherent sequence identity, homology, or similarity found in the family of proteins.

The term "binding affinity" includes the meaning of the strength of binding between an antibody molecule and an antigen.

By the term "immune cell" we mean any cell that is involved in a host immune or inflammatory response, including but not limited to B cells and T cells.

By the term "epithelial cell" we mean a cell of the epithelium. Epithelium is a tissue composed of a layer of cells. Epithelium can be found lining internal (e.g. endothelium, which lines the inside of blood vessels) or external (e.g. skin) free surfaces of the body.

The outermost layer of our skin is composed of squamous epithelial cells, as are the mucous membranes lining the inside of mouths and body cavities. Other epithelial cells line the insides of the lungs, the gastrointestinal tract, the reproductive and urinary tracts, and make up the exocrine and endocrine glands. Functions of epithelial cells include secretion, absorption and protection. Epithelial cells sit on a basal lamina.

PREFERRED EMBODIMENTS

Examples embodying certain preferred aspects of the invention will now be described with reference to the following figures in which:—

FIG. 1—scFv Isolated by Differential Whole Cell/Cell Membrane Vesicle Biopanning Show High Target Cell Specificity.

scFv clones isolated by differential biopanning were expressed in E. coli TOP10 cells and incubated with Ramos or Jurkat cells and (A) scFv clones expressed for primary screening or (B) seventy two randomly picked and re-expressed scFv clones. Bound scFv was detected with anti-His MAb, and Cy5-anti-mouse polyclonal Ab. Cell binding was detected in an FMAT Macroconfocal High Throughput Screening instrument. Cell binding is depicted as mean fluorescence intensity to target Ramos cells (Y axis) vs. non-target Jurkat cells (X-axis). (C) Binding of seven unique scFv clones to Ramos cells (filled bars) and Jurkat cells (open bars). A control scFv (ctrl) did not bind to any of the cells.

FIG. 2. Apoptosis Induction of Anti-Ramos scFv.

Ramos B lymphoma cells were sequentially incubated with anti-Ramos scFv, anti-His mAb, and anti-mouse polyclonal Ab on ice (with intermittent washing to remove excess unbound antibody), and were incubated in a humidified atmosphere of 5% $CO_2$ at 37° C. for 24 hours. Cells were then harvested and subjected to combined staining with Annexin V-AF488 (AV) and propidium iodide (PI). Cells were scored as viable (AV− PI−, filled circles FIG. 2C), early apoptotic (AV+ PI−, open triangles FIG. 2C), or late apoptotic/necrotic (AV+ PI+, open diamonds FIG. 2C), based on differential positively for AV and PI staining (defined by square gates in FIG. 2B). Results are presented by plotting (A) Forward Scatter (FSC-Height) against Side Scatter and (B) AV (FL-1) against PI (FL-3). The titratable effect of scFv B1 and F1 is also presented (C). The seven unique scFv clones were incubated with (D) Ramos or (E) Raji B lymphoma cells at 37° C. for 24 hours at various concentrations and the effect on apoptosis induction studied. Three scFv; B1, B11, and C11, show titratable activity towards both cell lines, whereas apoptosis inducing capability of scFv B10, C10, and G12 is restricted to Ramos B lymphoma cells.

Figure 3:
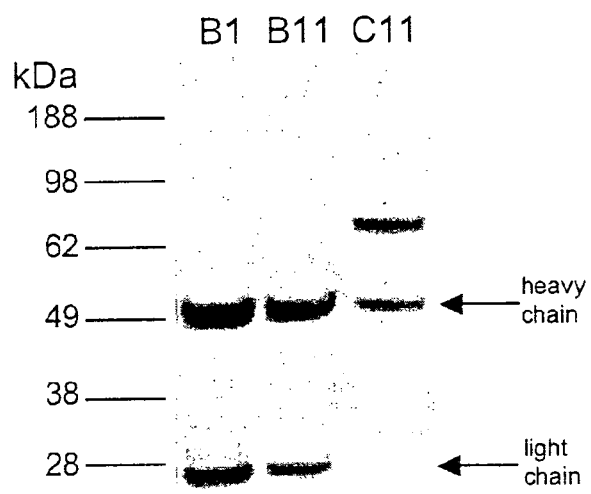
Figure 3:
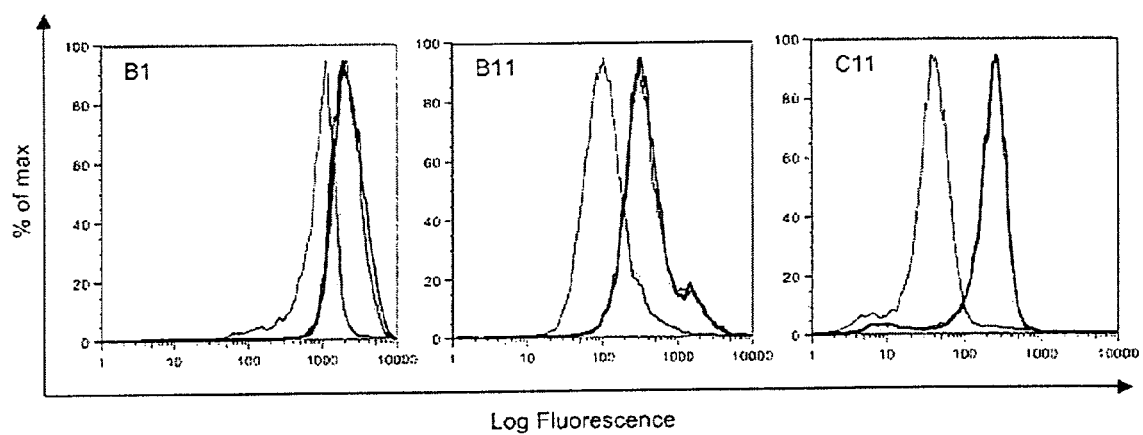

FIG. 3. Specificities of Isolated Antibodies Include HLA-DR/DP, IgM, and ICAM-1.

A) $50\text{-}600\times10^6$ Raji B lymphoma cells were lysed with the non-ionic detergent Triton X-100 at 0.5% v/v and immunoprecipitated with 100 µg of the fully human IgG1 format of B1 (lane 1) and B11 (lane 2) antibody, followed by crosslinking with Protein A Sepharose. Ramos B lymphoma cell lysates, from $50\times10^6$ cells, were used for the precipitation of 20 µg C11 (lane 3). Antibody-specific bands were excised and subjected to tryptic digestion and analysed by MALDI-TOF.

B) B1 IgG, B11 IgG, and C11 IgG binding to B lymphoma cells is specifically blocked by pre-incubation with anti-HLA-DR/DP, anti-ICAM-1 or anti-IgM antibodies, respectively.

To confirm the retrieved MALDI-TOF antigen identities of antibody clones B1, B11, and C11, blocking studies with commercially available antibodies was carried out and analyzed by flow cytometry. Cells were pre-blocked with 10-fold molar excess (compared to the human antibody) of species-matched blocking antibodies for 1 h, followed by the addition of any of the isolated human antibody clones. After 30 min, cells were washed and binding of human antibody to cells was detected by PE-conjugated goat anti-human IgG (Caltag Laboratories, Burlingame, Calif., USA). The blocking antibodies used in the study were; for B1, mouse monoclonals anti-HLA DR (Sigma, clone HK14) or anti-CD40 (Beckton Dickinson, clone 5C3); for B11, rabbit polyclonals anti-ICAM-1 (Abcam, ab7815-250) or anti-CD22 (Abcam, ab25135-100); for C11, goat polyclonals anti-IgM (Zymed, South San Francisco, Calif., USA, 62-7500) or anti-IgG (Zymed, 62-8400).

FIG. 4. ICAM-1 is a B Lymphoma Associated Cell Surface Receptor Capable of Mediating Programmed Cell Death.

A. 2 µg/ml of B11 or anti-FITC-8 (control) $IgG_1$ was added to $4\times10^5$ CL-01 B lymphoma cells, incubated for 2 h on ice, followed by addition of 10 µg/ml crosslinking secondary Fab'2 Goat anti-human Fc antibody. Cells were incubated at 37° C. for 6 h and the effect of the antibody incubation was determined by two independent apoptosis assays. Cells were stained either by AV/PI (upper panel), similarly as described above, or by incubation with 5 µg/ml of the mitochondrial membrane depolarization reagent JC-1 for 30 min at RT (lower panel). Induction of apoptosis is detectable by a decrease in the red (y-axis)/green (x-axis) fluorescence intensity ratio. (B) Histology section showing representative binding of B11 antibody to B lymphoma tissue. Cryo-preserved tissue obtained from a patient with Anaplastic Large Cell B Lymphoma was stained with B11 or FITC-8 (control) scFv antibody. Antibody binding was detected with DAB (brown colour). Inset picture shows staining with control scFv. (C) CD45-PerCp-Cy5.5 mAb pre-labelled Ramos cells were mixed with donor-derived PBMCs and the different cell populations were stained with fluorochrome-conjugated CD-specific antibodies and Alexa Flour 647 Zenon pre-labelled B11 IgG1 or control FITC-8 IgG1. IgG B11 binding to the different cell populations was recorded in the FL4 channel.

Figure 5:
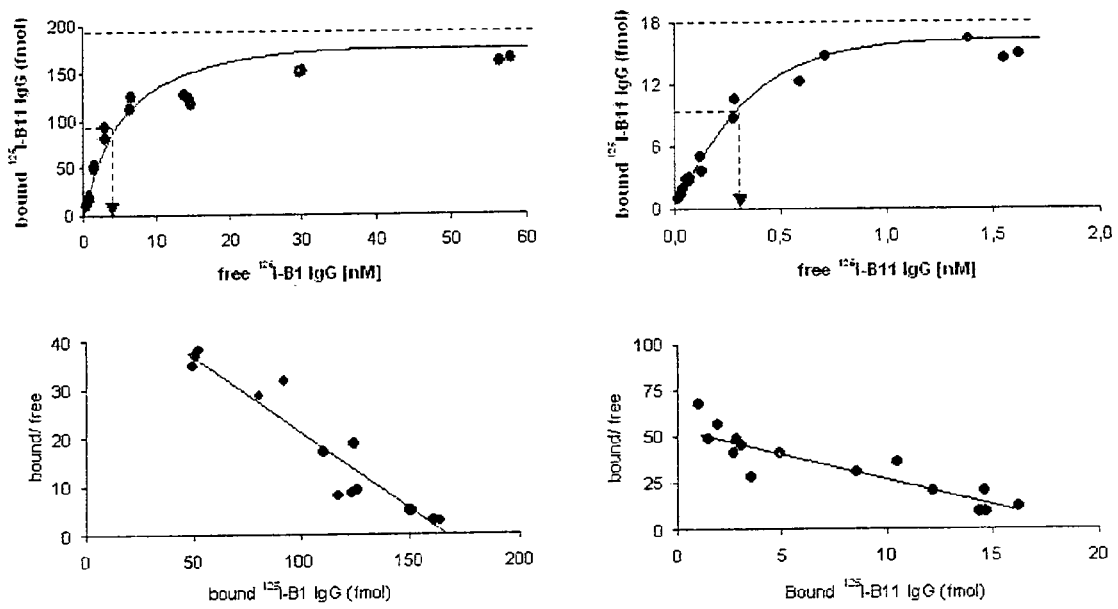

FIG. 5. Affinities of IgG B1 and IgG B11 to B lymphoma cells.

Raji cells (left panels, IgG B1) or Ramos cells (right panels, IgG B11) were incubated with increasing amounts of radioiodinated IgG B1 or radioiodinated IgG B11 protein in the presence or absence of 0.2 mg/ml of the corresponding unlabeled IgG protein. Specific binding was determined by subtracting binding in the presence of unlabeled competing protein from total binding. The amount of bound IgG B1 or IgG B11 protein increased with increasing amounts of free IgG protein with saturable binding being reached at ~30 nM IgG B1 and ~1 nM IgG B11, respectively (upper panels). Rosenthal-Scatchard plot analysis (lower panels) demonstrated a dissociation constant of 3 nM with 400,000 functional binding sites per Raji cell for IgG B1, and a dissociation constant of ~0.3 nM with 47,400 functional binding sites for IgG B11 (Raji cells).

Figure 6:
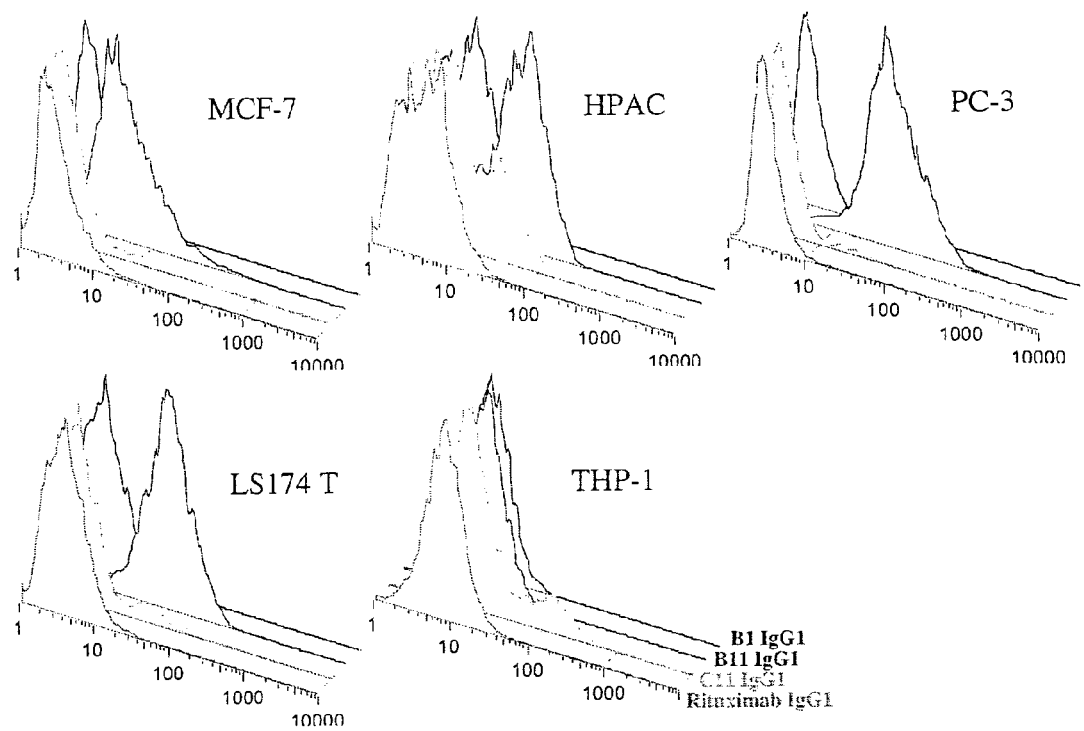

FIG. 6-B*inding* of B1, B11, C11 $IgG_1$ to tumour cell lines of different origin. The antigen distribution of antigens targeted by the B1, B11, and C11 antibodies on different carcinoma cell lines was investigated by flow-cytometry. Histograms show binding of Rituximab anti-CD20 Mab (first row front most peaks), B1 $IgG_1$ (second row peaks), B11 $IgG_1$ (third row peaks), or C11 $IgG_1$ (fourth row back most peaks) to MCF-7 breast carcinoma, HPAC pancreatic carcinoma, PC-3 prostate carcinoma, LS174 T colorectal carcinoma, and THP-1 monocytic leukaemia cells, as indicated.

FIG. 7—B11 $IgG_1$ Apoptosis Induction in Carcinoma Cells

The prostate carcinoma cell line PC-3 was grown in Complete Growth Medium (RPMI 1640, supplemented with 10% FCS, 10 mM HEPES, and 2 mM L-Glutamine) to 80% confluency in a 6 well plate. The prostate carcinoma cell line DU145 was grown in MEM with Earl's salts, supplemented with 10% FCS, 1 mM sodium pyruvate, and 1 mM non-essential amino acids and the derivate of a melanoma cell line MDA MB 435 was grown in DMEM supplemented with 10% FCS.

For apoptosis assays cells were washed in PBS and serially diluted B11 $IgG_1$ (or B1 $IgG_1$, Trastuzumab or negative antibody control for controls) was added to individual wells and binding was allowed during a 1-2 h incubation at 4° C. The cells were washed and Complete Growth Medium was added, containing crosslinking antibody, Fab'2 Goat anti-Human Fab'2, at 10 μg/ml. Cells were incubated in a humidified atmosphere, with 5% $CO_2$ at 37° C., for 16-24 hours. Cells were collected by trypsination and stained with Alexa Fluor 488-Annexin V (AF488-AV) and propidium iodide (PI), according to manufacturer's instructions. The percentage apoptotic cells was determined by the formula: % apoptotic cells=100−% AF488−AV/PI−/−.
  A) Contour plots show the relative distribution of PC-3 cells as a function of Annexin V and Propidium Iodide positivity following incubation as above with 2 μg/ml IgG B11 or IgG B1.
  B) Bar graph shows the mean percentage of apoptotic PC-3 cells following incubation with serially diluted B11 $IgG_1$ or 20 μg/ml B1 $IgG_1$.
  C) Bar graph shows the mean percentage of apoptotic MDA MB 435 cells following incubation with no antibody control, 10 μg/ml negative antibody control, serially diluted B11 $IgG_1$, or 10 μg/ml Trastuzuimb IgG1.
  D) Bar graph shows the mean percentage of apoptotic DU145 cells following incubation with no antibody control, 10 μg/ml negative antibody control, serially diluted B11 $IgG_1$, or 10 μg/ml Trastuzumb $IgG_1$ FIG. 8. B1 $IgG_1$ and B1 $IgG_4$ Induce Direct Cell Cytotoxicity on Raji B Lymphoma Cells in the Absence Of Cross-Linking Reagents.

Raji cells were incubated with B1 $IgG_1$, B1 $IgG_4$, Rituximab $IgG_1$, or control CT-17 $IgG_1$ at 20, 6.7 or 2.2 μg/ml for 24 hours. Cells were harvested and viability was determined as the percentage of Annexin V and Propidium Iodide double negative cells.

FIG. 9—VH and VL sequences (nucleotide and amino acid sequences for B1 antibody. SEQ ID NO:1 is the nucleotide sequence of B1-VH; SEQ ID NO:2 is the amino acid sequence of B 1-VH; SEQ ID NO:3 is the nucleotide sequence of B1-VL; and SEQ ID NO:4 is the amino acid sequence of B 1-VL.

FIG. 10—VH and VL sequences (nucleotide and amino acid sequences for B 11 antibody. SEQ ID NO:5 is the nucleotide sequence of B 11-VH; SEQ ID NO:6 is the amino acid sequence of B11-VH; SEQ ID NO:7 is the nucleotide sequence of B11-VL; and SEQ ID NO:8 is the amino acid sequence of B 11-VL.

FIG. 11—VH and VL sequences (nucleotide and amino acid sequences for C11 antibody. SEQ ID NO:9 is the nucleotide sequence of C11-VH; SEQ ID NO:10 is the amino acid sequence of C11-VH; SEQ ID NO:11 is the nucleotide sequence of C11-VL; and SEQ ID NO:12 is the amino acid sequence of C11-VL.

EXAMPLE 1

Selection and Screening (Biopanning) for Apoptosis Inducing Antibodies with Specificity for B Lymphoma Associated Cell Surface Receptors Cell Culture
The cell lines used in this study were obtained from ATCC (Manassas, Va., USA) or Deutsche Sammlung von Mikroorganismen und Zellkulturen (DSMZ) GmbH (Braunschweig, Germany) and were cultured in RPMI 1640 medium supplemented with 10% FCS, 2 mM L-Glutamine, 10 mM HEPES and 1 mM Na pyruvate (all from Invitrogen, Carlsbad, Calif., USA) unless otherwise stated. The Jurkat T leukaemia cell line (clone E6-1, TIB-152, ATCC), the B lymphoma cell lines DOHH-2 (ACC47, DSMZ), SC-1 (ACC558, DSMZ), WSU-NHL (ACC58, DSMZ), JVM-2 (ACC12, DSMZ), Jeko-1 (ACC553, DSMZ grown in 20% FCS), Rec-1 (ACC 584, DSMZ), SP-53 (Daibata et al. Cancer 1989; 64:1248-53), RL (CRL-2261, ATCC), Granta 519 (DSMZ), NCEB-1 (Saltman et al. Blood 1988; 72:2026-30), BJAB (Menezes et al. Biomedicine 1975; 22:276-84), Ramos (CRL-1596, ATCC), Raji (CCL-86, ATCC), Daudi (CCL-213, ATCC), CL-01 (Cerutti et al. J Immunol 1998; 160:2145-57), the pre B cell lymphoma KM-3/Reh (CRL-8286, ATCC) and the multiple myeloma MC/CAR (CRL-8083, ATCC, grown in IMDM (Invitrogen) supplemented with 20% FCS) were all free of mycoplasma and cultured in a humidified atmosphere at 37° C., using a 5% $CO_2$ atmosphere. The cells were maintained at $2\times10^5-1\times10^6$ cells/ml.

Jurkat Cell Membrane Vesicle Preparation
Jurkat cells were harvested by centrifugation at 300×g for 15 min in 500 ml buckets (Corning Inc. Life Sciences, New York, USA), washed in Dulbecco's PBS (Invitrogen), and resuspended in buffer A (1 mM $NaHCO_3$, 1.5 mM MgAc, pH 7.4). Cell concentration was approximately $5\times10^7$ Jurkat cells/ml ($5\times10^9$ cells in 100 ml Buffer A).

Cell disruption was achieved by hypo-osmotic shock treatment (Buffer A) on ice for 10-30 min and subsequent nitrogen cavitation in a Nitrogen cavitation bomb (Parr Instrument Company, Moline, Ill., USA). Cells were kept at a constant pressure of 40 bar (4,000 kPa) for 15 min at 0° C.

Disrupted cells were collected in a 250 ml Sarstedt tube (Sarstedt AG & Co, Nümbrecht, Germany) containing 500 μl 0.5 M EDTA to yield a final EDTA concentration of 2.5 mM. Addition of EDTA prevents aggregation of membrane vesicles. The homogenate (100 ml) was divided between 4×25 ml Beckman thick-walled rotor tubes (Beckman Coulter, Inc., Fullerton, Calif., USA), which were centrifuged for 10 min at 1900×g (4,000 rpm in an Sorvall SS34 rotor) at 4° C. to remove unbroken cells, nuclei, and heavy mitochondria.

The supernatant was collected and pelleted material was resuspended in 25 ml of 1 mM $NaHCO_3$ buffer containing 1 mM EDTA and was re-centrifuged (further recovery of pelleted crude Jurkat membranes). Jurkat membranes were pooled with membranes from the first centrifugation. Supernatants containing crude Jurkat membrane vesicles were ultra centrifuged using a Beckman Type 45Ti rotor at 40,000 rpm (approx. 200,000×g) for 2.5 h at 4° C. Supernatants were poured off and remaining buffer was removed by tipping the tube edge against a tissue (e.g. Kleenex™).

The crude membrane pellet was transferred to a Dounce homogeniser with the aid of a metal bar and was resuspended in 2.5 ml HES buffer (10 mM Hepes, 1 mM EDTA, 0.25 M sucrose, pH 7.4) by several careful strokes in the homogenizer. A membrane suspension concentration equivalent of $2\times10^9$ cells/ml containing 80-100 mg protein was, thus, achieved.

Selection of Phage Abs by Whole Cell/Cell Membrane Vesicle Competition Biopanning
Approximately $2\times10^{13}$ phage particles were pre-warmed at 37° C. for 15 min with intermittent mixing, centrifuged for 15 min at 14,000×g to remove precipitates, and the supernatant was transferred to a fresh Eppendorf tube. Non-fat dry milk was added to a final concentration of 2% (w/v). Jurkat membrane vesicle preparations derived from 2×10$^9$ cells (round 1 selection; 2×10$^8$ cells round 2 and 3 selections) were thawed on ice, and were mixed with the blocked phage particles. The mixture was incubated for 15 min on ice.

5×10$^7$ (5×10$^6$ 2$^{nd}$ and 3$^{rd}$ rounds) Ramos cells were harvested by centrifugation at 1,200 rpm for 6 min at 4° C. Supernatant was discarded and Ramos cells were resuspended in the milk-phage-Jurkat membrane vesicle mixture. The suspension was incubated at 10° C. under slow end-over-end rotation for 4 h.

The cell/cell membrane vesicle/phage mixture was transferred to a 15 ml Falcon tube (BD Biosciences, Bedford, Mass., USA), containing 0.5 ml 100% (trypan blue stained) Ficoll-Paque PLUS (Amersham Biosciences, Uppsala, Sweden) at the bottom, and 9.5 ml overlaid 40% (v/v) Ficoll in 2% (w/v) BSA/PBS (Ficoll-pillar). The tube was centrifuged at 1,500 rpm for 10 min at 4° C. The tube was removed from the centrifuge and the tube cap was screwed on and sealed airtight.

The bottom "tip" of the Falcon tube containing 100% Ficoll was chopped off using a cigar-chopper. Thus, very high-density material including membrane vesicle sheets and cell nuclei were eliminated from the tube. The tube cap was then carefully opened disrupting the vacuum inside the tube and allowing liquid to be expelled drop-wise through the opening at the (cut off) tube bottom.

The harvested cell suspension was washed once in PBS to remove excess Ficoll. The pellet was resuspended in 1 ml PBS (not performed following final wash) and the suspension was reloaded on top a fresh Ficoll-pillar and the washing procedure was repeated (twice in rounds 2 and 3).

Phage were eluted from cells by addition of 150 µl of 76 mM citric acid (pH 2.5) in PBS followed by incubation at room temperature for 5 min. The mixture was neutralized by addition of 200 µl of 1 M Tris-HCl, pH 7.4. Supernatants containing eluted phage were saved following pelleting of cells at 300×g for 5 min. Further elution of phage was by resuspension and incubation of the cell pellet in 1 ml trypsin at RT for 10 min.

Following inactivation with 40 µl 1 mg/ml aprotinin, cells were centrifuged and supernatant containing eluted phage was saved. Eluted phage were used to infect *Escherichia coli* HB101F' and the bacteria were plated on TB medium containing appropriate antibiotics and glucose. Bacterial colonies were counted, scraped from the plates, and used as inoculums for the next round of panning.

Conversion to scFv Format, scFv, Expression, Purification, and Analysis of Cell Binding The phagemid pool obtained following three rounds of selection was digested with EagI to remove the gene III. The resulting vector was re-ligated. Vectors containing re-ligated uncut gene III fragments were linearized by digestion with EcoRI enzyme. The scFv vector pool thus generated was used to transform *E. coli* TOP10 cells essentially as described earlier (Soderlind et al. Nat Biotechnol 2000; 18:852-6.).

Bacteria were plated on large 500 cm$^2$ agar plates and individual clones were picked, transferred to 96-well plates, and expressed in TB medium by over night culture at 37° C., 220 rpm using an automated system (Hallborn Biotechniques 2002; Suppl:30-7.). Recombinant scFv fragments were produced in TB medium containing appropriate antibiotics.

For primary screening of scFv clone binding to target Ramos cells and Jurkat non-target cells, 5,000 Ramos or Jurkat cells were incubated with either of 960 scFv clones, derived from the 3$^{rd}$ round of selection and produced as described above. Cells were incubated with 0.5 µg/ml anti-6×His mAb (R&D Systems, Minneapolis, Minn., USA) and 0.7 µg/ml Cy5-conjugated Goat anti-mouse reagent (Amersham Biosciences). Cell binding was analysed in an 8200 Cellular Detection System Fluorescence Macroconfocal High Throughput Screening (FMAT) instrument (Applied Biosystems, Foster City, Calif., USA).

Following primary screening, seventy two bacterial clones were picked randomly (i.e. irrespective of target cell vs. non-target cell reactivity in the primary screening) for DNA sequencing as described previously (Soderlind et al. Nat Biotechnol 2000; 18:852-6.) (Soderlind et al., 2000). For evaluation of cell surface binding by flow-cytometry, Ramos and Jurkat cells (both added at 2×10$^5$ cells per test) were incubated with individual scFv clones at a concentration of 2-10 µg/ml in PBS (Invitrogen) containing 0.5% w/v BSA (DPBS-B) for 1 h.

Cells were washed by centrifugation at 300×g for 6 min. Cells were then incubated with FITC-conjugated CD19 mAb and PE-conjugated CD3 mAb (BD) enabling subsequent identification of target and non-target cells, respectively. Detection of scFv binding was achieved by incubation with RPE-Cy5-streptavidin (Dako Cytomation, Glostrup, Denmark) following incubation with biotinylated anti-6×His mAb. Cells were incubated with secondary and tertiary reagents for 40 min, and 15 min respectively. All incubations were performed on ice using ice-cold solutions.

Differential Whole Cell/Cell Membrane Vesicle Panning

The present study utilized a novel panning protocol to isolate antibodies that target differentially expressed antigens in their native cell surface configuration. Following three rounds of competition biopanning, using whole Ramos B lymphoma cells and membrane vesicles derived from Jurkat T leukaemia cells, recombinant phage scFv were isolated. These were converted to soluble scFv and expressed in *E. coli* TOP10 cells.

Recombinant scFv were incubated with target (Ramos) or non-target (Jurkat) whole cells and examined for cell binding. The specificity for target cell antigens of the antibody clones was striking, since 482 scFv clones expressed were shown to bind selectively to Ramos target cells at intensities ranging from weak to very strong (FIG. 1A). Only two clones were identified that weakly stained non-target Jurkat cells (FIG. 1A).

We next determined the genotype diversity of isolated phage displayed scFv. Seventy-two scFv clones were randomly picked (i.e. irrespective of binding tropism as determined in the primary screening) for DNA sequencing.

The clones were simultaneously re-expressed and re-evaluated for target cell specificity (Ramos vs. Jurkat) by FMAT technology, as described (FIG. 1B). Seven different antibody genotypes were identified, as determined by their different CDRH3 and CDRL3 sequences (data not shown).

The high specificity of anti-Ramos scFv was confirmed by three colour flow-cytometric analysis, following incubation with equal numbers of Ramos and Jurkat cells and detection of scFv binding by means of anti-tag antibody (FIG. 1C).

Target and non-target cells were defined by CD19 and CD3 expression, respectively, using fluorochrome conjugated CD specific monoclonal antibodies. The seven genotypically unique scFv clones showed high and variable binding intensities to target Ramos cells, but no binding to the non-target Jurkat cells, as compared to the negative control scFv.

Apoptosis Assay

Lipopolysaccharide levels of recombinantly produced scFv fragments were reduced using Detoxigel columns according to manufacturer's instructions (Pierce Biotechnology, Rockford, Ill., USA). Remaining endotoxin levels were quantified by the LAL-amebocyte lysate assay (Cambrex Bioscience, Walkersville, Md., USA).

All scFv samples were found to contain less than 0.1 IU/ml of lipopolysaccharide. The chimeric anti-CD20 antibody Mabthera™ (Rituximab) was purchased from Lund University Hospital (Lund, Sweden). $2\times10^5$ B lymphoma cells (Raji or Ramos) or Jurkat T cells were incubated with serially diluted and detoxified scFv's in culture medium for 1 h on ice.

Cells were sequentially incubated with secondary anti-6× His mAb (5 µg/ml), and tertiary Goat Fab'2 anti-mouse Fab'2 antibody (Jackson ImmunoResearch Laboratories, Inc., West Grove, Pa., USA). Intermittent washings ensured removal of excess unbound antibody reagent. Cells were incubated at 37° C. in a humidified atmosphere of 5% $CO_2$ for 24 h.

When whole IgGs were used for apoptosis induction, crosslinking reagent was replaced by goat Fab'2 anti-human Fc γ antibody (Jackson ImmunoResearch) with minimal cross-reactivity with non-IgG antibody isotypes (to avoid unspecific crosslinking of endogenous B lymphoma associated surface immunoglobulins) and incubated, as described above, for 6 h.

Apoptotic cells were, unless otherwise stated, detected by combined staining with Annexin V Alexa Fluor 488 (AV) and Propidium Iodide (PI) (both from Molecular Probes, Invitrogen) and subsequent flow-cytometric analysis, Cells were defined as viable (AV−/PI−), early apoptotic (AV+/PI−) or late apoptotic/necrotic (AV+/PI+). AV and PI signals were recorded in the FL1 and FL2 or FL3 channels (as indicated in the text), respectively, using a FACSCalibur instrument (BD Biosciences).

In order to investigate the functionality of the isolated scFv we set up a high throughput apoptosis screening assay, based on sequential incubation and washing of cells with scFv and crosslinking reagent. The dependence on scFv clone and concentration in the apoptosis assay is demonstrated in FIG. 2 A-C, where the apoptotic effect of selected scFv clone B1 is compared to the—effect of scFv clone F1 which shows no induction of apoptosis. Jurkat cells lacking target antigen expression did not die from apoptosis after treatment with any of the examined scFv demonstrating that apoptosis induction depended on binding to target antigen (data not shown).

Using the established scFv-apoptosis assay, we screened clones for apoptosis on Ramos and Raji B lymphoma cells. scFv-induced apoptotic effects were compared to that induced by Rituximab anti-CD20 mAb (FIG. 2D). Three scFv clones—B1, B11 and C11—were identified that induced significant apoptosis on both Ramos and Raji cells (FIGS. 2 D and E). Induction of apoptosis by scFv on Raji cells correlated with binding to these cells (FIG. 2D), since scFv clones that failed to bind Raji cells did not induce apoptosis.

The B1, B11 and C11 clones were transferred to fully human IgG1 antibodies. Both their specificity and functionality remained intact after reformatting, as demonstrated by their strong binding and potent cytotoxicity towards a broad panel of B lymphoma cell lines (Table 1). Notably, apoptosis induction was rapid with maximal percentage of annexin V positive apoptotic cells being reached already after three to six hours in several cell lines (Table 1 and data not shown).

IgG Production and Endotoxin Screening Assays scFv antibody fragments were converted to full-length human IgG1λ format via cloning into a modified pcDNA3 vector (Norderhaug et al. J Immunol Methods 1997; 204:77-87.), and transiently transfected into HEK293 cells using Lipofectamine 2000 reagent according to manufacturer's instructions (Invitrogen).

Human IgG was purified from spent cultivation medium on a MabSelect protein A column (Amersham Biosciences). The purity of preparations was >98% as determined by SDS-PAGE analysis. Antibody preparations were screened and found to contain <0.1 IU/ml endotoxin at concentrations used in the present study, and as determined by the LAL amoebocyte lysate test (Cambrex Bioscience).

EXAMPLE 2

Analysis of Antibody Specificity

Antigen Identification

The identity of the targeted antigens was determined by immunoprecipitation of B lymphoma cell lysates. Cells (50-600×$10^6$ per ml lysis buffer, depending on antibody and cell line) were harvested by centrifugation, washed twice in PBS and incubated for 15 min in Lysis Buffer (25 mM Tris-HCl, pH 7.5, 150 mM NaCl, 5 mM EDTA, and Complete EDTA-free Protease inhibitor cocktail (Roche Diagnostics GmbH, Mannheim, Germany)) containing the detergent Triton X-100 (Sigma-Aldrich, St. Louis, Mo., USA) at 0.5% v/v.

Cellular debris was spun down at 16,000×g for 15 min in a conventional table-top centrifuge and the soluble proteins were pre-cleared with Protein A Sepharose 4 Fast Flow (Amersham Biosciences) (¹/₁₀ volume of reaction) for 1 h on rotation. For every sample, 1 ml of pre-cleared cell lysate was immunoprecipitated for 2 h by 20-100 µg of any of the human antibodies. Protein A Sepharose 4 Fast Flow was added again and incubated for 30 min, where after the immuno-complexes were washed extensively in lysis buffer, boiled for 5 min. and finally resuspended in Sample Buffer (1× NuPAGE LDS Sample Buffer, 1× NuPAGE Sample Reducing Agent) and separated in a NuPAGE Novex 4-12% Bis-Tris Gel (all from Invitrogen).

After staining (Simply Blue Safestain, Invitrogen), protein bands of interest were excised from the SDS-PAGE and subjected to tryptic digestion, as described (Edvardsson et al. Electrophoresis 1999; 20:935-42.).

Briefly, gel plugs were destained and equilibrated by washing three times with 200 µl 50% acetonitril (ACN) under agitation. After drying in a SpeedVac concentrator (Savant, Farmingdale, N.Y., USA) for 15 min, samples were reduced by addition of 25 µl 10 mM DTT/100 mM $NH_4HCO_3$ and incubated for 56° C. for 1 h and alkylated by addition of 25 µl 55 mM iodoacetamide/100 mM $NTH_4HCO_3$ followed by incubation for 45 min at room temperature.

After two additional 10 min washing steps in 100 mM $NH_4HCO_3$ followed by one wash in 50% v/v ACN, the gel pieces were dried in a SpeedVac concentrator and re-swelled and digested in 15 µl of 15 ng/µl trypsin (Promega Corporation, Madison, Wis., USA) in 25 mM $NH_4HCO_3$ at 37° C. over night. Peptides were extracted by addition of 50% v/v ACN/1% v/v TFA and 10 min incubation at RT. 1 µl of the extract was spotted onto MALDI sample plates and allowed to dry. 1 µl matrix solution (5 mg/ml alpha-cyano-4-hydroxy cinnamic acid (CHCA) in 75% v/v ACN/1% v/v TFA) was spotted on top of the peptides.

Peptide masses were determined using an Applied Biosystems 4700 Maldi Workstation. The proteins were identified by peptide mass fingerprint database searching using Mascot search tools (Matrixscience, UK). Antigen specificities of clones B10, C10, and G12 were identified using similar methodology, except scFv's and anti-His coated magnetic microbeads (Miltenyi Biotec GmbH, Bergisch Gladbach, Germany) were used for immunoprecipitations.

Following conversion to the full antibody format B1, B11 and C11 IgG were used to precipitate antigens from Raji and Ramos B lymphoma cells. IgG B1 precipitated two bands of approximately 28 and 34-kDa, respectively (FIG. 3A, lane 1). Gel slices containing these bands were prepared and digested with trypsin and analysed by mass spectrometry identifying HLADR/DP as the target antigen.

The specificity of IgG B1 for HLA-DR/DP was verified both by western blotting and detection of HLA-DR/DP protein, using a commercially available monoclonal antibody, and by blocking of B1 IgG binding following pre-incubation of cells with a commercially available HLA-DR specific monoclonal antibody (FIG. 3B).

The identities of the IgG B11 and C11 defined antigens were established using similar methodology. IgG C11 was found to precipitate a 68 kDa protein band identified as the membrane bound form of the B cell receptor μ chain (FIG. 3A, lane 3). IgG11 precipitated a 90 kDa protein band that was identified as the intercellular cell adhesion molecule-1 (ICAM-1) (FIG. 3A, lane 2). The specificities of IgG B11 for ICAM-1, and of C11 IgG for IgM, were confirmed by MS-MS analysis, antibody blocking studies (FIG. 3B), and western blot analysis (data not shown) using commercially available antibodies.

Specificities of clones B10, C10, and G12 were determined, using scFv and anti-H is coated magnetic microbeads for immunoprecipitation. The three scFv clones precipitated a protein band of 68 kDa, and MS-analysis of trypsin digested gel slices containing these bands revealed their specificity for surface IgM. Presumably, these antibodies recognize the Ramos IgM idiotype, since neither of them cross-react with peripheral blood B lymphocytes or other IgM positive B cell lines.

EXAMPLE 3

Analysis of Antibody Affinities

In Vitro Iodination of B1 and B11 Immunoglobulins

Iodination of 1 mg/ml of $IgG_1$ B1 or $IgG_1$ B11 proteins with [$^{125}$I] NaI was performed in PBS for 10 min using Iodogen pre-coated iodination tubes (Pierce). Free [$^{125}$I] NaI was removed by desalting on PD-10 columns (Amersham Biosciences), yielding specific radioactivities in the range of 100-1600 cpm per ng protein. [$^{125}$I] $IgG_1$ B1 and [$^{125}$I] $IgG_1$ B11 was used for determination of antibody affinities.

Determination of IgG B1 and IgG B11 Affinity Constants

Radioiodinated IgG B1 or IgG B11 was incubated with B lymphoma cells in DPBS-B-hIgG (DPBS-B containing 0.2 mg/ml human IgG) for 2 h on ice with intermittent mixing. Non-specific binding was determined in the presence of 0.2 mg/ml unlabeled IgG B1 or IgG B11 protein, as appropriate. Analysis was performed in triplicates.

Cells were loaded on top 40% v/v Ficoll/DPBS-B cushions in individual tubes and were centrifuged at 400×g for 6 min at 4° C. Samples were frozen at −80° C. Cell pellets and cell supernatants were isolated and analysed separately for $^{125}$I-IgG protein content in a gamma counter, following cutting of the tubes in half.

Antibody affinity constants (Kd values) and epitope numbers per cell were determined from Scatchard plot analysis according to Rosenthal et al (Anal Biochem 1967; 20:525-32), Bylund and Yamamura (Methods in Neurotransmitter Analysed. New York: Raven Press Ltd., 1990), and Marquardt (J. Soc. Indust. Appl. Math 1963; 11:431-41), as previously described (Brix et al. J. Clin. Invest. 1998; 102:283-93).

IgG B1 and IgG B11 binding to HLA-DR and ICAM-1 was characterised by incubating the radio-iodinated proteins with Raji or Ramos cells in the presence or absence of 0.2 mg/ml of the corresponding unlabeled IgG protein at 4° C. The specific binding of [$^{125}$I] IgG to the cell surface was calculated by subtracting non-specific binding (binding in the presence of excess unlabeled IgG) from the total binding.

Saturation of specific IgG B1 binding to Raji cells was reached at ~30 nM IgG B1 (FIG. 5). Rosenthal-Scatchard plot analysis revealed a dissociation constant of ~3 nM with 400,000 functional binding sites per Raji cell, assuming a bivalent epitope-IgG interaction (FIG. 5). Similarly, the dissociation constant of IgG B11 was determined to ~0.2 nM with 47,400 receptors per Ramos cell.

TABLE 1

Fully human B1, B11 and C11 IgG antibodies show dynamic binding patterns and induce apoptosis in various B lymphoma cell lines.

| | | Antibody clone -- specificity | | | | | | | |
|---|---|---|---|---|---|---|---|---|---|
| | | B1 - HLA DR/DP | | B11 - ICAM-1 | | C11 - IgM | | Rituximab - CD20 | |
| Tumor classification | Cell line | MFI[b] | Apoptosis Induction[a] | MFI | Apoptosis Induction | MFI | Apoptosis Induction | MFI | Apoptosis Induction |
| Follicular Lymphoma | DOHH-2 | 140 | − | 100 | − | 90 | − | 480 | ++ |
| | WSU-NHL | 280 | + | 0 | − | 60 | − | 790 | + |
| | SC-1 | 170 | + | 0 | − | 50 | − | 50 | − |
| | RL | 50 | − | 100 | − | 210 | − | 200 | + |
| Mantle cell Lymphoma | Granta 519 | 370 | ++ | 260 | + | 60 | + | 360 | +++ |
| | JVM-2 | 650 | + | 100 | − | 10 | − | 520 | + |
| | Rec-1 | 0 | − | 380 | − | 900 | − | 580 | + |
| | SP-53 | 500 | ++ | 90 | − | 360 | − | 740 | ++ |
| | NCEB-1 | 750 | + | 340 | + | 10 | − | 430 | + |
| | Jeko-1 | 1000 | +++ | 30 | + | 1040 | ++ | 1160 | +++ |
| Burkitt's Lymphoma | Ramos | 125 | + | 100 | ++ | 240 | +++ | 300 | +++ |
| | Raji | 550 | +++ | 420 | + | 20 | + | 400 | + |
| | Daudi | 200 | + | 150 | + | 450 | + | 480 | ++ |
| | BJAB | 530 | + | 310 | + | 510 | + | 530 | ++ |
| | CL-01 | 940 | +++ | 600 | ++ | 60 | + | 970 | ++ |

TABLE 1-continued

Fully human B1, B11 and C11 IgG antibodies show dynamic binding patterns and induce apoptosis in various B lymphoma cell lines.

| | | Antibody clone -- specificity | | | | | | |
|---|---|---|---|---|---|---|---|---|
| | | B1 - HLA DR/DP | | B11 - ICAM-1 | | C11 - IgM | | Rituximab - CD20 | |
| Tumor classification | Cell line | MFI[b] | Apoptosis Induction[a] | MFI | Apoptosis Induction | MFI | Apoptosis Induction | MFI | Apoptosis Induction |
| pre B cell Leukaemia | Reh/KM-3 | 240 | +++ | 20 | − | 0 | − | 0 | − |
| Multiple Myeloma | MC/CAR | 290 | ++ | 120 | + | 0 | − | 110 | − |

[a] Apoptosis Induction; determined by percentage of viable cells after 6 hour incubation with any of the human antibodies, crosslinked with Goat anti-Human (gamma) Fc specific antibody; −, viability not affected; +, 95-80%; ++, 79-60%; +++, 59-40% viable cells compared to control (human FITC-8 IgG$_1$). The results are based on duplicate samples in three independent experiments.
[b] MFI; Mean Fluorescence Intensity of secondary RPE-conjugated Goat anti-Human IgG antibody. The cell line dependent MFI value of control human FITC-8 IgG antibody was subtracted from the MFI of each human antibody.

EXAMPLE 4

ICAM-1 is a B Lymphoma Associated Antigen with Apoptosis Inducing Properties

Flow-Cytometric Analysis of IgG Binding to Ramos Cells

Ramos cells (13×10$^6$) were stained with CD45-PerCp-Cy5.5 mAb by incubation on ice for 45 min, washed in DPBS-B, and kept on ice until mixing with unlabeled purified PBLs.

Buffy coats from two healthy volunteers were obtained from the Lund University Hospital. Buffy coats were diluted 1:2 in PBS and washed by centrifugation at 500×g (1500 rpm Beckman Spinchron centrifuge) for 10 min, complete aspiration of the supernatant and resuspension in DPBS containing 1% heat inactivated FCS (DPBS-HI). Washing was repeated twice. Red blood cells were lysed by incubation with red blood cell lysing solution (BD Biosciences) for 15 min at RT. Cells were washed by centrifugation at 60×g (667 rpm Beckman spinchron centrifuge) for 10 min and the supernatant was carefully aspirated. Cells were counted in a Bürker chamber following staining with trypan blue reagent (Invitrogen) and exclusion of dead cells, washed in DPBS-HI, pelleted, and resuspended in DPBS-B containing 200 µg/ml human purified IgG (blocking of Fc receptors).

For each donor and test condition, approximately 2.5×10$^6$ leukocytes were mixed with 1.6×10$^5$ PerCpCy5.5 pre-labelled Ramos cells. Mouse monoclonal CD3-FITC, CD56-PE, and CD19-PerCpCy5.5 antibodies (BD Biosciences) were added and the mixtures were incubated on ice until addition of labelled human IgG. Labelling of n-CoDeR human IgG antibodies and positive control anti-CD20 mouse-human chimeric antibody Rituximab with AF647 Fab fragments (Molecular Probes, Invitrogen) was performed according to manufacturer's instructions.

Briefly, 4 µg of each of IgG B1, B11, C11, and Rituximab antibodies were incubated with 20 µl of AF647-Fab labelling reagent for 5 min at RT. Following addition of 20 µl human IgG blocking reagent and a further incubation for 5 min, AF647-labeled IgG was three-fold serially diluted in DBPS-B, and diluted IgG proteins were added to the mixed Ramos/PBL cell solutions.

Samples were incubated for 1 h, washed, resuspended in DPBS-B, and analysed for binding to different cell subpopulations by flow-cytometry, following appropriate calibration and compensation of the instrument for four-colour analysis. Ramos cells were identified as the PerCpCy5.5$^{high}$ population distinct from the B lymphocyte PerCpCy5.5$^{low}$ population.

Immunohistochemistry

Cryopreserved lymph node biopsies of patients with Anaplastic Large Cell B lymphoma (one patient), Centroblastic/Centrocytic B non-Hodgkin lymphoma (three patients), and B cell chronic lymphocytic leukaemia (one patient) were obtained from the Department of Pathology at Lund University (Lund, Sweden). Eight-micrometer sections of cryo-preserved tissue were fixed in acetone for 10 min at 4° C. Endogenous biotin-binding activity was blocked by sequential treatment with Avidin and Biotin (Avidin/Biotin blocking kit, Invitrogen) for 20 min each.

Tissues were incubated with 5 µg/ml control scFv or B11 scFv for 1 h. Following washing, sections were incubated with biotin-conjugated mouse anti-His mAb (R&D Systems) for 30 min. scFv binding was detected following treatment with ABC Complex/HRP reagent (Dako Cytomation) for 30 min, and subsequent incubation with DAB for 5 min.

Sections were photographed using a Leica DC 300F digital camera mounted on top of a Leica DMR light/fluorescence microscope.

Handling of human tissue followed the recommendation of the local Ethics Committee at Lund University Hospital.

Mitochondrial Membrane Depolarization Assay

Mitochondrial membrane depolarization was analysed as previously described (Kim et al. Mol Biol Cell 2004; 15:420-34). Briefly, antibody-treated cells were mixed with JC-1 reagent (Molecular Probes) at 5 µg/ml and incubated for 30 min at RT. Cells were washed twice in ice-cold PBS and resuspended in 300 µl PBS and analysed on a FACS Aria (BD Biosciences). The green and red fluorescence was collected through 494/518 nm (FL-1) and 595/615 nm (FL-2) bandpass filters, respectively.

ICAM-1 is a glycoprotein of the immunoglobulin superfamily (Marlin et al. Cell 1987; 51:813-9) capable of inducing bi-directional signalling (Rothlein et al. J Immunol 1994; 152:2488-95; Vyth-Dreese et al. Blood 1995; 85:2802-12). ICAM-1 has not previously been demonstrated to be involved in programmed death in B lymphoma cells.

Therefore, we wanted to confirm that IgG B11 induced cell death was an active process, by means other than cell membrane phosphatidyl serine translocation.

Mitochondrial membrane depolarization was chosen as a validation of apoptosis, since this is a common feature of caspase dependent and caspase independent apoptosis that may be monitored by cell staining with 5,5',6,6'-tetrachloro-1,1',3,3'-tetraethylbenzimidazolyl-carbocyanine iodide (JC-1 reagent).

In accordance with our Annexin V/propidium iodide assay (FIG. 4A, upper panel), IgG B11 was found to induce mitochondrial membrane depolarization in CL-01 B lymphoma cells, as determined by flow-cytometric analysis following staining with JC-1 reagent (FIG. 4A, lower panel).

In order to exclude the possibility that ICAM-1 expression was an in vitro artifact, resulting from a general up-regulation during cell culture, we examined the binding of IgG B11 to tissue obtained from five different patients with different B lymphoma tumours.

By immunohistochemistry, IgG B11 showed strong binding to the five lymphoma tissues (FIG. 4B), at intensities comparable to, or slightly lower than, the anti-HLA-DR/DP antibody IgG B1 (Table 2).

We next examined the binding of IgG B11 to B lymphoma versus resting peripheral blood leukocytes. Ramos was chosen as a representative B lymphoma cell line, based on its low-end epitope expression yet significant sensitivity to B11 induced apoptosis. Flow-cytometric analysis, following mixed incubation of pre-labelled Ramos cells with whole blood peripheral blood leukocytes and either of IgG B1, B11 or C11 antibodies, revealed that IgG B11 showed strong binding to Ramos cells.

Even more importantly, B11 demonstrated the greatest differential binding (strongest antigen up-regulation) of the three antibodies to Ramos B lymphoma cells versus normal peripheral blood leukocytes (FIG. 4C. and data not shown). IgG B11 binding peaked already at 0.1 µg/ml and was 3.7-fold up regulated on Ramos versus monocyte cells (MFI 654 versus 176), 8.3-fold up regulated on Ramos versus peripheral blood B lymphocytes (MFI 654 versus 78), and 23-fold up regulated compared to NK cells. Binding to other monitored peripheral blood leukocyte subsets was negative.

TABLE 2

ICAM-1 is strongly expressed in B lymphoma tissue of different origin

| Patient | | Antibody clone - specificity | |
|---|---|---|---|
| ID | Tumour classification | B11-ICAM-1 | B1-HLA-DR/DP |
| A | B-CLL[c] (low malignant non-Hodgkin Lymphoma) | + | ++ |
| B | Anaplastic Large Cell B Cell Lymphoma | ++ | +++ |
| C | Centroblastic-Centrocytic B non-Hodgkin Lymphoma | ++/+++ | ++ |
| D | B-CLL/B-PLL[d] | ++ | +++ |
| E | Centroblastic B non-Hodgkin Lymphoma | ++/+++ | +++ |
| F | Centroblastic-Centrocytic B non-Hodgkin Lymphoma | ++ | +++ |

[c]B-CLL = B- Chronic Lymphocytic Leukemia,
[d]B-PLL = B- Pro Lymphocytic Leukemia.
Increasing numbers of + indicate stronger staining.

EXAMPLE 5

Antigen Distribution of B1, B11, C11 IgG$_1$ on Tumour Cell Lines of Various Origins, as Determined by Flow Cytometry The antigen distribution of human antibody targeted antigens, mainly for B11, on different carcinoma cell lines was investigated. Cells (MCF-7 and MDA MB 435S breast carcinoma, JAR and JEG-3 chorio-carcinoma, A549 lung carcinoma, TCC-SUP urinary bladder carcinoma, MDA MB 435 melanoma, HPAC, PANC-1 and BxPC-3 pancreatic carcinoma, PC-3 and DU145 prostate carcinoma, LS174 T, CaCO$_2$, and Lovo colorectal carcinoma, and THP-1 monocytic leukaemia cells), were washed in PBS, and resuspended at $4 \times 10^6$ cells/ml in Complete Medium (200,000 cells/50 µl sample). B1 IgG$_1$, B11 IgG$_1$, C11 IgG$_1$, negative control FITC-8 IgG$_1$, and Rituximab anti-CD20 mAb was 3-10-fold serially diluted (10-0.1 pg/ml) in Complete Medium (50 µl/sample). Cells were incubated with either of the antibodies for 1 hour on ice, washed by resuspension in PBS/BSA 0.5%, centrifuged at 1200 rpm for 5 min, and complete aspiration of the supernatants was undertaken. Cells were incubated with PE-conjugated Goat F(ab')2 anti-Human IgG (Caltag Laboratories, Cat no: H10104), diluted 1/50 in PBS/BSA 0.5%, for 30 min, on ice. Following resuspension of in 300 µl PBS/BSA 0.5%, cells were analysed for IgG binding using a FACScan instrument.

PC-3 prostate carcinoma cells showed strong expression of ICAM-1 as demonstrated by the strong binding of B11 IgG to these cells (FIG. 6). MCF-7 breast carcinoma, HPAC pancreatic carcinoma, and LS174 T colorectal carcinoma cells were also found to express ICAM-1 albeit at lower intensity compared to the prostate cancer cells. In contrast, THP-1 monocytic leukaemia cells did not express ICAM-1. All carcinoma cell lines initially tested were found negative for CD20, HLA-DR/DP, and IgM expression as demonstrated by the lack of binding of Rituximab IgG, B1 IgG, and C11 IgG, respectively. Further studies on additional carcinoma cells lines indicated that all carcinoma cells examined were positive for ICAM-1 expression (Table 3).

TABLE 3

ICAM-1 is strongly expressed in carcinoma cell lines of different origin

| Tumor cell type | Cell line | MFI |
|---|---|---|
| Chorio-carcinoma | JAR | 2000 |
|  | JEG-3 | 1600 |
| Prostate carcinoma | DU145 | 2200 |
|  | PC-3 | 1500 |
| Pancreatic carcinoma | BxPC-3 | 2000 |
|  | PANC-1 | 3800 |
| Colon carcinoma | CaCo2 | 800 |
|  | Lovo | 1600 |
| Lung carcinoma | A549 | 800 |
| Urinary bladder carcinoma | TCC-SUP | 3200 |
| Melanoma | MDA MB 435 | 4000 |
| Mammary carcinoma | MDA MB 435S | 800 |

EXAMPLE 6

B11 IgG$_1$ Apoptosis Induction in Carcinoma Cells

B11 IgG$_1$ was shown in example 5 to bind strongly to carcinoma cells. The present example examined the apoptosis inducing properties of this antibody on carcinoma cells.

Cells were seeded in 6 well plates with Complete Growth Medium three days before the onset of the experiment. Cells were between 50-75% confluent at the time of the experiment. Cells were washed with ice-cold PBS and incubated with serially diluted (20-0.02 µg/ml as indicated in the figures, in 1 ml Complete Growth Medium) B11 IgG$_1$, 20 µg/ml control B1 IgG$_1$, 10 µg/ml negative control IgG$_1$ or 10 µg/ml Trastuzumab IgG$_1$ as indicated at 4° C. for 1-2 hours. Cells were washed with ice-cold PBS and secondary F(ab'2) Goat anti-Human F(ab'2) antibody (diluted in Complete Growth Medium to 10 µg/ml) was added. Cells were incubated at 37° C., in a humidified atmosphere of 5% $CO_2$ for 16-24 hours. Total cells were collected by first isolating the supernatant, followed by PBS wash and trypsination of remaining adherent cells. The enzymatic reaction was terminated by resuspension in PBS containing 10% heat-inactivated fetal calf serum. Cells were washed in ice-cold PBS, subjected to Annexin V/propidium iodide staining, and analysed for viability/apoptosis as described in example 5 above.

The B11 $IgG_1$ was shown to induce apoptosis in the carcinoma cell lines in a specific and titratable manner (FIG. 7). Control IgG B1, which did not bind to PC-3 cells (see example 5), also did not induce apoptosis in PC-3 cells. Negative control $IgG_1$ or Trastuzumab $IgG_1$ were not able to induce apoptosis in DU145 or MDA MB435 cells.

EXAMPLE 7

Pharmaceutical Formulations and Administration

A further aspect of the invention provides a pharmaceutical formulation comprising a compound according to the first aspect of the invention in admixture with a pharmaceutically or veterinarily acceptable adjuvant, diluent or carrier.

Preferably, the formulation is a unit dosage containing a daily dose or unit, daily sub-dose or an appropriate fraction thereof, of the active ingredient.

The compounds of the invention will normally be administered orally or by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, the compounds of the invention can be administered alone but will generally be administered in admixture with a suitable pharmaceutical excipient, diluent or carrier selected with regard to the intended route of administration and standard pharmaceutical practice.

For example, the compounds of the invention can be administered orally, buccally or sublingually in the form of tablets, capsules, ovules, elixirs, solutions or suspensions, which may contain flavouring or colouring agents, for immediate-, delayed- or controlled-release applications. The compounds of the invention may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The compounds of the invention can also be administered parenterally, for example, intravenously, intra-arterially, intraperitoneally, intrathecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human patients, the daily dosage level of the compounds of the invention will usually be from 1 mg/kg to 30 mg/kg. Thus, for example, the tablets or capsules of the compound of the invention may contain a dose of active compound for administration singly or two or more at a time, as appropriate. The physician in any event will determine the actual dosage, which will be most suitable for any individual patient, and it will vary with the age, weight and response of the particular patient. The above dosages are exemplary of the average case. There can, of course, be individual instances where higher or lower dosage ranges are merited and such are within the scope of this invention.

The compounds of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" delivers an appropriate dose of a compound of the invention for delivery to the patient. It will be appreciated that the overall daily dose with an aerosol will vary from patient to patient, and may be administered in a single dose or, more usually, in divided doses throughout the day.

Alternatively, the compounds of the invention can be administered in the form of a suppository or pessary, or they may be applied topically in the form of a lotion, solution, cream, ointment or dusting powder. The compounds of the invention may also be transdermally administered, for example, by the use of a skin patch. They may also be administered by the ocular route, particularly for treating diseases of the eye.

For ophthalmic use, the compounds of the invention can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Generally, in humans, oral or topical administration of the compounds of the invention is the preferred route, being the most convenient. In circumstances where the recipient suffers from a swallowing disorder or from impairment of drug absorption after oral administration, the drug may be administered parenterally, e.g. sublingually or buccally.

For veterinary use, a compound of the invention is administered as a suitably acceptable formulation in accordance with normal veterinary practice and the veterinary surgeon will determine the dosing regimen and route of administration, which will be most appropriate for a particular animal.

---

The invention claimed is:

1. An isolated human monoclonal antibody molecule or fragment thereof that selectively binds to ICAM-1 on the surface of a target cell and, on binding ICAM-1, induces apoptosis of the target cell, wherein the antibody or fragment has variable regions having the sequences set forth in SEQ ID NOs: 6 and 8.

2. The isolated antibody molecule of claim 1 wherein the target cell is an immune cell or an epithelial cell.

3. The isolated antibody molecule of claim 2 wherein the immune cell is a B lymphocyte.

4. The isolated antibody molecule of claim 1 wherein the target cell is associated with a disease.

5. The isolated antibody molecule of claim 4 wherein the disease is selected from the group consisting of: cancer; autoimmune diseases; an acute inflammatory disorder; a chronic inflammatory disorder; sepsis and infectious disease, wherein said autoimmune diseases are selected from the group consisting of rheumatoid arthritis, and Systemic lupus erythematosus (SLE).

6. The isolated antibody molecule of claim 5 wherein the disease is a cancer selected from lymphoma, leukaemia, myeloma, gastric cancer, breast cancer, liver cancer, lung cancer, melanoma, bladder cancer, choroid cancer, pancreatic cancer, colon cancer and prostate cancer.

7. The isolated antibody molecule of claim 1 wherein the antibody molecule is an IgG.

8. The antibody molecule of claim 7 wherein the antibody is a single chain antibody selected from the group of an IgG$_1$, IgG$_2$, IgG$_3$ or IgG$_4$.

9. A pharmaceutical composition comprising a human monoclonal antibody molecule or a fragment thereof, and a pharmaceutically-acceptable carrier, excipient or diluent, wherein said antibody molecule or fragment selectively binds to ICAM-1 on the surface of a target cell, and on binding ICAM-1, induces apoptosis of the target cell, wherein the antibody or fragment has variable regions having the sequences set forth in SEQ ID NOs: 6 and 8.

10. The isolated antibody of claim 5, wherein said infectious disease is HIV.

11. A method of inducing apoptosis in a target cell comprising the steps:
  a. providing one or more target cells displaying the cell surface antigen, ICAM-1;
  b. providing a human monoclonal antibody molecule or fragment thereof which selectively binds to cell surface ICAM-1 and, on binding ICAM-1, induces apoptosis of the target cell, wherein the antibody or fragment has variable regions having the sequences set forth in SEQ ID NOs: 6 and 8; and
  c. exposing the target cells of (a) to the antibody molecule or fragment of (b) to induce apoptosis in the target cells.

12. An in vitro method of inducing apoptosis in a target cell comprising the steps of:
  a. providing one or more target cells;
  b. providing a human monoclonal antibody molecule or fragment thereof that selectively bind to cell surface ICAM-1 of said target cells, wherein the antibody or fragment has variable regions having the sequences set forth in SEQ ID NOs: 6 and 8; and
  c. exposing the target cells of (a) to the antibody molecule or fragment of (b) so as to induce apoptosis in the target cells.

13. An in vitro method as claimed in claim 12 wherein the target cells provided in step (a) are immune cells or epithelial cells.

14. An in vitro method as claimed in claim 13 wherein the immune cells are B-lymphocytes.

15. An in vitro method as claimed in claim 14 wherein the disease is a cancer selected from lymphoma, leukaemia, myeloma gastric cancer, breast cancer, liver cancer, lung cancer, melanoma, bladder cancer, choroid cancer, colon cancer, and prostate cancer.

16. An in vivo method of inducing apoptosis in a target cell comprising the steps of:
  a. providing one or more target cells;
  b. providing one or more human monoclonal antibody molecules or fragments thereof that selectively bind to cell surface ICAM-1 of said target cells, wherein the antibody or fragment has variable regions having the sequences set forth in SEQ ID NOs: 6 and 8; and
  c. exposing the target cells of (a) to the antibody molecules or fragments of (b) so as to induce apoptosis in the target cells.

17. An in vivo method as claimed in claim 16 wherein the target cells provided in step (a) are immune cells or epithelial cells.

18. An in vivo method as claimed in claim 17 wherein the immune cells are B-lymphocytes.

19. An in vivo method as claimed in claim 16 wherein the disease is a cancer selected from lymphoma, leukaemia, myeloma, gastric cancer, breast cancer, liver cancer, lung cancer, melanoma, bladder cancer, choroid cancer, pancreatic cancer, colon cancer and prostate cancer.

* * * * *

UNITED STATES PATENT AND TRADEMARK OFFICE
CERTIFICATE OF CORRECTION

PATENT NO.         : 7,943,744 B2
APPLICATION NO.    : 12/097193
DATED              : May 17, 2011
INVENTOR(S)        : Björn Frendéus et al.

It is certified that error appears in the above-identified patent and that said Letters Patent is hereby corrected as shown below:

On Title Page, Item (75), Inventors, please delete "Roland Carlsson, Lund (SE); Anne-Christine Carlsson, legal representative, Lund (SE)" and insert --Roland Carlsson, deceased, late of Lund (SE); by Anne-Christine Carlsson, legal representative, Lund (SE)-- therefor;

On Title Page, Item (56), References Cited, Other Publications, Mac Callum, Martin, and Thornton reference, please delete "interations" and insert -- interactions-- therefor;

On Title Page, Item (56), References Cited, Other Publications, De Pascalis, Iwahashi, Tamura, Padlan, Gonzales, Santos, Giuliano, Schuck, Schlom, and Kashmiri reference, please delete "humanzied" and insert --humanized-- therefor;

Column 33, line 45 (Claim 8), after "The" please insert --isolated--;

Column 33, line 56 (Claim 10), after "antibody" please insert --molecule--.

Signed and Sealed this
Eleventh Day of October, 2011

David J. Kappos
*Director of the United States Patent and Trademark Office*

SEQUENCE LISTING

```
<160> NUMBER OF SEQ ID NOS: 12

<210> SEQ ID NO 1
<211> LENGTH: 351
<212> TYPE: DNA
<213> ORGANISM: Homo sapiens

<400> SEQUENCE: 1
gaggtgcagc tgttggagtc tgggggaggc ttggtacagc ctgggggtc cctgagactc      60 tcctgtgcag cctctggatt caccttagc agctatgcca tgagctgggt ccgccaggct     120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac actgccgtgt attactgtgc gagagatggg    300
ctactacccc ttgactactg gggccagggt acactggtca ccgtgagctc a             351

<210> SEQ ID NO 2
<211> LENGTH: 117
<212> TYPE: PRT
<213> ORGANISM: Homo sapiens

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Leu Leu Pro Leu Asp Tyr Trp Gly Gln Gly Thr Leu
```

Val Thr Val Ser Ser
        115

<210> SEQ ID NO 3
<211> LENGTH: 336
<212> TYPE: DNA
<213> ORGANISM: Homo sapiens

<400> SEQUENCE: 3

```
cagtctgtgc tgactcagcc accctcagcg tctgggaccc ccgggcagag ggtcaccatc    60
tcttgttctg gaggcagctc aacatcgga gggaatgctg taaattggta tcagcagctc   120
ccaggaacgg cccccaaact cctcatctat gaaaataata agcgaccctc aggggtccct   180
gaccgattct ctggctccaa gtctggcacc tcagcctccc tggccatcag tgggctccgg   240
tccgaggatg aggctgatta ttactgcagc tcatatgcgg tcagcaacaa tttcgaggtg   300
ctattcggcg gaggaaccaa gctgacggtc ctaggt                             336
```

<210> SEQ ID NO 4
<211> LENGTH: 112
<212> TYPE: PRT
<213> ORGANISM: Homo sapiens

<400> SEQUENCE: 4

Gln Ser Val Leu Thr Gln Pro Pro Ser Ala Ser Gly Thr Pro Gly Gln
1               5                   10                  15

Arg Val Thr Ile Ser Cys Ser Gly Gly Ser Ser Asn Ile Gly Gly Asn
            20                  25                  30

Ala Val Asn Trp Tyr Gln Gln Leu Pro Gly Thr Ala Pro Lys Leu Leu
        35                  40                  45

Ile Tyr Glu Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ser Ser Tyr Ala Val Ser Asn
                85                  90                  95

Asn Phe Glu Val Leu Phe Gly Gly Gly Thr Lys Leu Thr Val Leu Gly
            100                 105                 110

<210> SEQ ID NO 5
<211> LENGTH: 351
<212> TYPE: DNA
<213> ORGANISM: Homo sapiens

<400> SEQUENCE: 5

```
gaggtgcagc tgttggagtc tgggggaggc ttggtacagc ctggggggtc cctgagactc    60
tcctgtgcag cctctggatt caccttcagt aacgcctgga tgagctgggt ccgccaggct   120
ccagggaagg ggctggagtg gtggcattt atatggtatg atggaagtaa taatactat    180 gcagactccg tgaagggccg attcaccatc tccagagaca attccaagaa cacgctgtat   240
ctgcaaatga acagcctgag agccgaggac actgccgtgt attactgtgc gagatacagt   300
ggctggtact ttgactactg gggccaaggt acactggtca ccgtgagctc a            351
```

<210> SEQ ID NO 6
<211> LENGTH: 117
<212> TYPE: PRT
<213> ORGANISM: Homo sapiens -continued

```
<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ala Phe Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ser Gly Trp Tyr Phe Asp Tyr Trp Gly Gln Gly Thr Leu
            100                 105                 110

Val Thr Val Ser Ser
        115

<210> SEQ ID NO 7
<211> LENGTH: 336
<212> TYPE: DNA
<213> ORGANISM: Homo sapiens

<400> SEQUENCE: 7
cagtctgtgc tgactcagcc accctcagcg tctgggaccc ccgggcagag ggtcaccatc    60
tcctgcactg ggagcagctc caacatcggg gcaggttatg atgtacactg gtatcagcag   120
ctcccaggaa cggcccccaa actcctcatc tatgataaca acaatcggcc ctcaggggtc   180
cctgaccgat tctctggctc caagtctggc acctcagcct ccctggccat cagtgggctc   240
cggtccgagg atgaggctga ttattactgc cagtcctatg acagcagcct cagtgcttgg   300
ctgttcggcg gaggaaccaa gctgacggtc ctaggt                             336

<210> SEQ ID NO 8
<211> LENGTH: 112
<212> TYPE: PRT
<213> ORGANISM: Homo sapiens

<400> SEQUENCE: 8

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Asn Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Ser Ser
                85                  90                  95

Leu Ser Ala Trp Leu Phe Gly Gly Gly Thr Lys Leu Thr Val Leu Gly
            100                 105                 110

<210> SEQ ID NO 9
<211> LENGTH: 360
<212> TYPE: DNA
<213> ORGANISM: Homo sapiens
```

-continued

<400> SEQUENCE: 9

```
gaggtgcagc tgttggagtc tgggggaggc ttggtacagc ctggggggtc cctgagactc    60
tcctgtgcag cctctggatt caccttcggc agttatgaaa tgaactgggt ccgccaggct   120
ccagggaagg ggctggagtg gtctcagtt atttatagcg gtggtagcac atactacgca   180
gactccgtgg aaggccgatt caccatctcc agagacaatt ccaagaacac gctgtatctg   240
caaatgaaca gcctgagagc cgaggacact gccgtgtatt actgtgcgag agatacaaac   300
ccgtactact actacggtat ggacgtctgg ggccaaggta cactggtcac cgtgagctca   360
```

<210> SEQ ID NO 10
<211> LENGTH: 120
<212> TYPE: PRT
<213> ORGANISM: Homo sapiens

<400> SEQUENCE: 10

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Glu Met Asn Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Glu
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Thr Asn Pro Tyr Tyr Tyr Gly Met Asp Val Trp Gly Gln
            100                 105                 110

Gly Thr Leu Val Thr Val Ser Ser
        115                 120
```

<210> SEQ ID NO 11
<211> LENGTH: 333
<212> TYPE: DNA
<213> ORGANISM: Homo sapiens

<400> SEQUENCE: 11

```
cagtctgtgc tgactcagcc accctcagcg tctgggaccc ccgggcagag ggtcaccatc    60
tcctgttctg gaagcagctc caacatcgga aataatgctg taaactggta tcagcagctc   120
ccaggaacgg ccccccaaact cctcatctat aggaataatc agcggccctc aggggtccct   180
gaccgattct ctggctccaa gtctggcacc tcagcctccc tggccatcag tgggctccgg   240
tccgaggatg aggctgatta ttactgccag tcctatgaca gcagcctgaa tggtcaagta   300
ttcggcggag gaaccaagct gacagtccta ggt                                333
```

<210> SEQ ID NO 12
<211> LENGTH: 111
<212> TYPE: PRT
<213> ORGANISM: Homo sapiens

<400> SEQUENCE: 12

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30
```

-continued

```
Ala Val Asn Trp Tyr Gln Gln Leu Pro Gly Thr Ala Pro Lys Leu Leu
         35                  40                  45

Ile Tyr Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

Asn Gly Gln Val Phe Gly Gly Gly Thr Lys Leu Thr Val Leu Gly
                100                 105                 110
```